US008116472B2

(12) United States Patent
Mizuno

(10) Patent No.: US 8,116,472 B2
(45) Date of Patent: Feb. 14, 2012

(54) NOISE CONTROL DEVICE

(75) Inventor: Ko Mizuno, Kyoto (JP)

(73) Assignee: Panasonic Corporation, Osaka (JP)

( * ) Notice: Subject to any disclaimer, the term of this patent is extended or adjusted under 35 U.S.C. 154(b) by 995 days.

(21) Appl. No.: 12/088,045

(22) PCT Filed: Oct. 18, 2006

(86) PCT No.: PCT/JP2006/320769
§ 371 (c)(1), (2), (4) Date: Mar. 25, 2008

(87) PCT Pub. No.: WO2007/046435
PCT Pub. Date: Apr. 26, 2007

(65) Prior Publication Data

US 2010/0150367 A1 Jun. 17, 2010

(30) Foreign Application Priority Data

Oct. 21, 2005 (JP) ................................ 2005-306904

(51) Int. Cl.
*A61F 11/06* (2006.01)
*G10K 11/16* (2006.01)
*H03B 29/00* (2006.01)

(52) U.S. Cl. ...................... 381/71.1; 381/71.6; 381/71.7

(58) Field of Classification Search ......... 381/71.1–71.8
See application file for complete search history.

(56) References Cited

U.S. PATENT DOCUMENTS 4,953,217 A * 8/1990 Twiney et al. ............... 381/71.6
5,182,774 A * 1/1993 Bourk .......................... 381/71.6
5,604,813 A 2/1997 Evans et al.
5,715,321 A * 2/1998 Andrea et al. .................. 381/92
5,995,631 A * 11/1999 Kamada et al. .................... 381/1
7,353,908 B1 * 4/2008 French .......................... 181/206
2005/0276422 A1 * 12/2005 Buswell et al. ............ 381/71.14

FOREIGN PATENT DOCUMENTS

JP 02-224498 9/1990
JP 06-327087 11/1994

(Continued)

OTHER PUBLICATIONS

International Search Report mailed Feb. 6, 2007 for International Application No. PCT/JP2006/320769.

(Continued)

*Primary Examiner* — Anh Mai
(74) *Attorney, Agent, or Firm* — Wenderoth, Lind & Ponack, LLP

(57) ABSTRACT

A noise control device reduces noises respectively arriving in a plurality of spaces which are acoustically independent from each other. The noise control device includes sound output devices, which are respectively provided in the plurality of spaces so as to respectively correspond to the plurality of spaces, each for outputting a sound to a corresponding space. The noise control device also includes a noise detection device, which is provided in at least one of the plurality of spaces, for detecting a noise arriving in the at least one of the plurality of spaces. Further, the noise control device includes a signal generation device which is a single device for generating, based on the noise detected by one noise detection device, a cancellation signal for canceling the noise, and outputting the generated cancellation signal to each of the plurality of sound output device.

11 Claims, 26 Drawing Sheets

FOREIGN PATENT DOCUMENTS

| | | |
|---|---|---|
| JP | 07-219558 | 8/1995 |
| JP | 09-160567 | 6/1997 |
| JP | 9-505677 | 6/1997 |
| JP | 2001-016679 | 1/2001 |
| JP | 2005-257720 | 9/2005 |
| WO | 94/17512 | 8/1994 |
| WO | 95/30221 | 11/1995 |

OTHER PUBLICATIONS

Ascii Corp., Monthly ASCII, 2005, The May issue, Apr. 18, 2005, ISSN0386-5428, p. 99, "Reduce the Noise for Comfortable Listening Environment! Two Types of Noise Cancellation Headphones" w/translation.

* cited by examiner

WHEN DETECTION SIGNAL OF LEFT EAR MICROPHONE 14a IS USED

NOISE CONTROL DEVICE

TECHNICAL FIELD

The present invention relates to a noise control device, and particularly to a noise control device for reducing noises respectively arriving in a plurality of spaces which are acoustically independent from each other.

BACKGROUND ART

In recent years, a so-called noise-canceling headphone has entered the market in response to the growing needs of improvement in comfortability in an environment where there is too much noise, typically an aircraft cabin or the like. The noise-canceling headphone is a headphone apparatus using an active noise control technique in which a control sound in antiphase to a noise is actively outputted, whereby the noise is reduced (e.g., Patent Document 1).

Hereinafter, a conventional noise-canceling headphone will be described with reference to FIG. 20. FIG. 20 shows a configuration of the conventional noise-canceling headphone. Here, FIG. 20 shows a view seen from above a head of a user 90. In FIG. 20, the user 90 faces upward.

As shown in FIG. 20, the noise-canceling headphone comprises a headband 91, a left ear case 92*a*, a right ear case 92*b*, a left ear speaker 93*a*, a right ear speaker 93*b*, a left ear microphone 94*a*, a right ear microphone 94*b*, a left ear control section 95*a* and a right ear control section 95*b*. The left ear case 92*a* is placed near a left ear of the user 90. The right ear case 92*b* is placed near a right ear of the user 90. The left ear case 92*a* and the right ear case 92*b* are connected by the headband 91. The left ear speaker 93*a* is provided within the left ear case 92*a*. The right ear speaker 93*b* is provided within the right ear case 92*b*. The left ear microphone 94*a* is provided within the left ear case 92*a*. The right ear microphone 94*b* is provided within the right ear case 92*b*.

Here, the left ear case 92*a* and the right ear case 92*b* have spaces formed therein, respectively. These spaces are acoustically independent from each other. Here, being acoustically independent means that an acoustic state is such that a gain of an electroacoustic transfer function between the spaces is sufficiently small.

The left ear microphone 94*a* detects a noise arriving in the left ear case 92*a*. The left ear microphone 94*a* outputs, as a detection signal $e_L$ to the left ear control section 95*a*, a noise signal based on the detected noise. The left ear control section 95*a* generates, based on the detection signal $e_L$, a control signal for controlling a level of the detection signal $e_L$ such that the level is lowered. The left ear control section 95*a* outputs the generated control signal to the left ear speaker 93*a*. Similarly, the right ear microphone 94*b* detects a noise arriving in the right ear case 92*b*. The right ear microphone 94*b* outputs, as a detection signal $e_R$ to the right ear control section 95*b*, a noise signal based on the detected noise. The right ear control section 95*b* generates, based on the detection signal $e_R$, a control signal for controlling a level of the detection signal $e_R$ such that the level is lowered. The right ear control section 95*b* outputs the generated control signal to the right ear speaker 93*b*.

Next, configurations of the left ear control section 95*a* and the right ear control section 95*b* as well as processes performed by the left ear control section 95*a* and the right ear control section 95*b* will be described in detail with reference to FIG. 21. FIG. 21 shows, by blocks of signal processing, the configuration of the noise-canceling headphone of FIG. 20. It is assumed for FIG. 21 that components, which are denoted by the same reference numerals as those used for components in FIG. 20, have the same functions as those of the components in FIG. 20, and descriptions thereof will be omitted.

A block 921*a* in the left ear case 92*a* indicates an electroacoustic transfer function $H_L$ from an input of the left ear speaker 93*a* to an output of the left ear microphone 94*a*. A block 921*b* within the right ear case 92*b* indicates an electroacoustic transfer function $H_R$ from an input of the right ear speaker 93*b* to an output of the right ear microphone 94*b*. An adder 922*a* adds an output signal of the block 921*a* to a noise signal $N_L$ indicating the noise arriving in the left ear case 92*a*. A signal outputted from the adder 922*a* is the aforementioned detection signal $e_L$. An adder 922*b* adds an output signal of the block 921*b* to a noise signal $N_R$ indicating the noise arriving in the right ear case 92*b*. A signal outputted from the adder 922*b* is the aforementioned detection signal $e_R$.

First, a process performed for the left ear of the user 90 will be described. The left ear control section 95*a* comprises a feedback control filter 951*a* and a phase inverter 952*a*. For the feedback control filter 951*a*, a filter coefficient indicating a transfer function $C_L$ is set. The detection signal $e_L$ outputted from the adder 922*a* is inputted to the feedback control filter 951*a*. The phase inverter 952*a* inverts a phase of an output signal of the feedback control filter 951*a*. An output signal from the phase inverter 952*a* is inputted to the block 921*a*. Here, a transfer function from the noise signal $N_L$ to the detection signal $e_L$ is represented by an equation (1).

(equation 1)

$$\frac{e_L}{N_L} = \frac{1}{1 + C_L H_L} \tag{1}$$

Here, the transfer function $C_L$ of the feedback control filter 951*a* is set, as shown in an equation (2), so as to have an inverse characteristic to that of the electroacoustic transfer function $H_L$ at the left ear. Note that, a indicates a filter gain of a fixed frequency.

(equation 2)

$$C_L = \frac{\alpha}{H_L} \tag{2}$$

When the noise arrives in the left ear case 92*a*, the left ear microphone 94*a* outputs, as is clear from the equation (1), $N_L/(1+C_L \times H_L)$ as the detection signal $e_L$. The detection signal $e_L$ is inputted to the feedback control filter 951*a*. At this point, the control signal generated at the feedback control filter 951*a* is $C_L \times N_L/(1+C_L+H_L)$. Since the transfer function $C_L$ is set as shown in the equation (2), the control signal is $N_L/(H_L \times (1+1/\alpha))$. The control signal is inputted to the block 921*a* after a phase of the control signal is inverted at the phase inverter 952*a*. Accordingly, a cancellation sound, which is $-H_L \times N_L/(H_L \times (1+1/\alpha)) = -N_L/(1+1/\alpha)$, is radiated from the left ear speaker 93*a* to the vicinity of the left ear. As a result, the greater the filter gain α, the nearer to $-N_L$ the cancellation sound becomes, whereby the noise arriving near the left ear is canceled.

Next, a process performed for the right ear of the user 90 will be described. The right ear control section 95*b* comprises a feedback control filter 951*b* and a phase inverter 952*b*. For the feedback control filter 951*b*, a filter coefficient indicating a transfer function $C_R$ is set. The detection signal $e_R$ outputted from the adder 922*b* is inputted to the feedback control filter

951$b$. The phase inverter 952$b$ inverts a phase of an output signal of the feedback control filter 951$b$. An output signal from the phase inverter 952$b$ is inputted to the block 921$b$. Note that, the process performed for the right ear is different from the above-described process performed for the left ear only in that the transfer function $C_R$ of the right ear control section 95$b$ has an inverse characteristic to that of the electroacoustic transfer function $H_R$ at the right ear. Other than this, the process performed for the right ear is the same as that of the process performed for the left, and therefore a description thereof will be omitted.

There is a known conventional technique in which the noise reduction function illustrated in FIG. 21 and an audio signal outputting function are combined. FIG. 22 shows a configuration in which the noise reduction function and the audio signal outputting function are combined. It is assumed for FIG. 22 that components, which are denoted by the same reference numerals as those used for components in FIG. 20, have the same functions as those of the components in FIG. 20, and descriptions thereof will be omitted.

A configuration shown in FIG. 22 is a result of adding, to the configuration shown in FIG. 20, an audio signal output section 97, a left ear audio signal canceling section 98$a$, a right ear audio signal canceling section 98$b$, subtractors 99$a$ and 99$b$, and adders 100$a$ and 100$b$. The audio signal output section 97 outputs audio signals such as music. As shown in FIG. 22, the audio signal output section 97 outputs an audio signal $A_L$ to the left ear and an audio signal $A_R$ to the right ear. The left ear audio signal canceling section 98$a$ generates, based on a filter coefficient indicating a transfer function simulating the electroacoustic transfer function $H_L$, a cancellation signal for canceling the audio signal $A_L$. The subtractor 99$a$ subtracts, from the detection signal $e_L$, the cancellation signal for canceling the audio signal $A_L$. An output signal from the subtractor 99$a$ is inputted to the left ear control section 95$a$. A control signal outputted from the left ear control section 95$a$ is added to the audio signal $A_L$ by the adder 100$a$. An output signal from the adder 100$a$ is inputted to the left ear speaker 93$a$. The left ear speaker 93$a$ outputs a sound based on the control signal and the audio signal $A_L$.

Here, the detection signal $e_L$ from the left ear microphone 94$a$ contains the audio signal $A_L$. However, the subtractor 99$a$ subtracts, from the detection signal $e_L$, the cancellation signal for canceling the audio signal $A_L$. As a result, the audio signal $A_L$ is not inputted to the left ear control section 95$a$, and the same process as that described in FIG. 21 is performed at the left ear control section 95$a$.

The right ear audio signal canceling section 98$b$ generates, based on a filter coefficient indicating a transfer function simulating the electroacoustic transfer function $H_R$, a cancellation signal for canceling the audio signal $A_R$. The subtractor 99$b$ subtracts, from the detection signal $e_R$, the cancellation signal for canceling the audio signal $A_R$. An output signal from the subtractor 99$b$ is inputted to the right ear control section 95$b$. A control signal outputted from the right ear control section 95$b$ is added to the audio signal $A_R$ by the adder 100$b$. An output signal from the adder 100$b$ is inputted to the right ear speaker 93$b$. The right ear speaker 93$b$ outputs a sound based on the control signal and the audio signal $A_R$. Other than the above, the process for the right ear is the same as the above-described process for the left ear, and therefore a description thereof will be omitted. As described above, the configuration shown in FIG. 22 allows noise reduction and stereo audio signal reproduction to be performed concurrently.

Usually, in a radio frequency band, a phase lag occurs in each of the electroacoustic transfer functions $H_L$ and $H_R$. For this reason, there is a problem that even if, e.g., the transfer function $C_L$ is set to have an inverse characteristic to that of the electroacoustic transfer function $H_L$, the transfer function $C_L$ does not have the inverse characteristic to that of the electroacoustic transfer function $H_L$ in the radio frequency band, whereby noise reduction effect deteriorates. For this problem, there is a conventionally suggested configuration as shown in FIG. 23 for widening a frequency band in which a noise reduction effect is obtained. FIG. 23 shows a configuration of a noise-canceling headphone capable of widening a frequency band in which a noise reduction effect is obtained. The configuration shown in FIG. 23 is a result of adding, to the configuration shown in FIG. 20, a left ear high frequency control section 101$a$, a right ear high frequency control section 101$b$ and adders 102$a$ and 102$b$.

As shown in FIG. 23, the left ear control section 95$a$ generates, based on the detection signal $e_L$, a control signal for controlling a level of the detection signal $e_L$ such that the level is lowered, the control signal having a frequency which is no higher than a predetermined frequency. In other words, the left ear control section 95$a$ generates a cancellation signal for canceling a noise arriving in the left ear case 92$a$, the noise having the frequency which is no higher than the predetermined frequency. Here, the predetermined frequency is lower than a frequency at which a phase lag of the electroacoustic transfer function $H_L$ occurs. The left ear control section 95$a$ outputs the generated control signal to the adder 102$a$. The left ear high frequency control section 101$a$ generates, based on the detection signal $e_L$, a control signal for controlling the level of the detection signal $e_L$ such that the level is lowered, the control signal having a frequency which is higher than the predetermined frequency. In other words, the left ear high frequency control section 101$a$ generates a cancellation signal for canceling a noise arriving in the left ear case 92$a$, the noise having the frequency which is higher than the predetermined frequency. The left ear high frequency control section 101$a$ outputs the generated control signal to the adder 102$a$. The adder 102$a$ adds the control signal generated at the left ear control section 95$a$ to the control signal generated at the left ear high frequency control section 101$a$. A signal resulting from the addition at the adder 102$a$ is inputted to the left ear speaker 93$a$. The left ear speaker 93$a$ outputs sounds based on the control signals generated at the left ear control section 95$a$ and the left ear high frequency control section 101$a$. As a result, the sounds, which are based on the control signals, and the noises are canceled by each other near the left ear.

On the other hand, the right ear control section 95$b$ generates, based on the detection signal $e_R$, a control signal for controlling a level of the detection signal $e_R$ such that the level is lowered, the control signal having a frequency which is no higher than a predetermined frequency. In other words, the right ear control section 95$b$ generates a cancellation signal for canceling a noise arriving in the right ear case 92$b$, the noise having the frequency which is no higher than the predetermined frequency. Here, the predetermined frequency is lower than a frequency at which a phase lag of the electroacoustic transfer function $H_R$ occurs. The right ear control section 95$b$ outputs the generated control signal to the adder 102$b$. The right ear high frequency control section 101$b$ generates, based on the detection signal $e_R$, a control signal for controlling the level of the detection signal $e_R$ such that the level is lowered, the control signal having a frequency which is higher than the predetermined frequency. In other words, the right ear high frequency control section 101$b$ generates a cancellation signal for canceling a noise arriving in the right ear case 92$b$, the noise having a frequency which is higher than the predetermined frequency. The right ear high frequency control section 101*b* outputs the generated control signal to the adder 102*b*. The adder 102*b* adds the control signal generated at the right ear control section 95*b* to the control signal generated at the right ear high frequency control section 101*b*. A signal resulting from the addition at the adder 102*b* is inputted to the right ear speaker 93*b*. The right ear speaker 93*b* outputs sounds based on the control signals generated at the right ear control section 95*b* and the right ear high frequency control section 101*b*. As a result, the sounds, which are based on the control signals, and the noises are canceled by each other near the right ear.

As described above, separately for a high frequency band higher than the predetermined frequency in which a phase lag of the electroacoustic transfer function occurs, controls are performed using the left ear high frequency control section 101*a* and the right ear high frequency control section 101*b* for each of which a filter coefficient is set based on the electroacoustic transfer function whose phase is lagged. This allows a frequency band, in which the noise reduction effect is obtained, to be widened.

[Patent Document 1] (PCT) International Publication WO94/17512

SUMMARY OF THE INVENTION

Problems to be Solved by the Invention

As described above, in a headphone apparatus or the like, a space formed within the left ear case 92*a* and a space formed within the right ear case 92*b* are acoustically independent from each other. For this reason, it is usual in the conventional manner that control is separately performed for each of the right ear and the left ear. Therefore, in the above-described conventional noise-canceling headphone, the control for the left ear is performed by the left ear control section 95*a* and the control for the right ear is performed by the right ear control section 95*b*.

Described here is a case where processing at the left ear control section 95*a* and processing at the right ear control section 95*b* are performed by two arithmetic processing circuits (not shown). These arithmetic processing circuits are CPUs, for example. When the processing is performed by two arithmetic processing circuits, there is a problem of increasing costs due to the necessity to provide the two arithmetic processing circuits.

In order to reduce the costs, it is conceivable to perform the processing at the left ear control section 95*a* and right ear control section 95*b* by a single arithmetic processing circuit. In this case, however, the amount of arithmetic processing to be performed increases as compared to the case where two arithmetic processing circuits are provided. For this reason, input/output delays at the left ear control section 95*a* and the right ear control section 95*b* increase. This consequently causes a problem that the above-described noise reduction effect to be obtained is extremely reduced.

Therefore, an object of the present invention is to provide a noise control device, which is capable of sufficiently producing the noise reduction effect without increasing an input/output delay at a control section even in the case where the processing is performed by a single arithmetic processing circuit.

Solution to the Problems

A first aspect of the present invention is a noise control device for reducing noises respectively arriving in a plurality of spaces which are acoustically independent from each other. The noise control device comprises: a plurality of sound output means, which are respectively provided in the plurality of spaces so as to respectively correspond to the plurality of spaces, each for outputting a sound to a corresponding space; first noise detection means, which is provided in at least one of the plurality of spaces, for detecting a noise arriving in the at least one of the plurality of spaces; and first signal generation means which is a single means for generating, based on the noise detected by one of the first noise detection means, a cancellation signal for canceling the noise, and outputting the generated cancellation signal to each of the plurality of sound output means.

In a second aspect of the present invention based on the above first aspect, the first signal generation means generates the cancellation signal such that a level of the cancellation signal increases in accordance with a decrease in a frequency of the cancellation signal.

In a third aspect of the present invention based on the above first aspect, the noise control device further comprises: second noise detection means, provided in a space which is not one of the plurality of spaces and in which a noise source generating the noise is present, for detecting the noise arriving from the noise source; and second signal generation means for generating, based on the noise detected by the second noise detection means, a cancellation signal for canceling the noise, and outputting the generated cancellation signal to each of the plurality of sound output means.

In a fourth aspect of the present invention based on the above first aspect, a plurality of the first noise detection means are provided in the plurality of spaces, respectively. The noise control device further comprises third signal generation means, which are provided respectively corresponding to the plurality of the first noise detection means, each for generating, based on the noise detected by a corresponding one of the first noise detection means, the cancellation signal having a higher frequency than a predetermined frequency, and outputting the generated cancellation signal to one of the sound output means which is provided in a same space as that of the corresponding one of the first noise detection means. The first signal generation means generates, based on the noise detected by one of the plurality of first noise detection means, the cancellation signal having a frequency no higher than the predetermined frequency, and outputs the generated cancellation signal to each of the plurality of sound output means.

In a fifth aspect of the present invention based on the above fourth aspect, the predetermined frequency is lower than a frequency at which a phase lag occurs in an electroacoustic transfer function from an input of each sound output means to an output of a corresponding one of the first noise detection means which is provided in a same space as that of said each sound output means.

In a sixth aspect of the present invention based on the above first aspect, a plurality of the first noise detection means are provided in the plurality of spaces, respectively. The noise control device further comprises switching means for switching, among outputs of the plurality of the first noise detection means, an output of first noise detection means to which an input of the first signal generation means is to be connected. In accordance with an operation by a user, the switching means switches the output of the first noise detection means to which the input of the first signal generation means is to be connected, to an output of first noise detection means which is most closely provided to the noise source generating the noise.

In a seventh aspect of the present invention based on the above first aspect, a plurality of the first noise detection means are provided in the plurality of spaces, respectively. The noise control device further comprises: switching means for switching, among outputs of the plurality of the first noise detection means, an output of first noise detection means to which an input of the first signal generation means is to be connected; and level detection means for detecting a level of the noise detected by each of the plurality of the first noise detection means. The switching means switches the output of the first noise detection means to which the input of the first signal generation means is to be connected, to an output of first noise detection means for which a highest level has been detected by the level detection means.

In an eighth aspect of the present invention based on the above first aspect, a plurality of the first noise detection means are provided in the plurality of spaces, respectively. The noise control device further comprises: switching means for switching, among outputs of the plurality of the first noise detection means, an output of first noise detection means to which an input of the first signal generation means is to be connected; and calculation means for calculating a cross-correlation function for noises respectively detected by the plurality of the first noise detection means. The switching means switches the output of the first noise detection means, based on the cross-correlation function calculated by the calculation means.

In a ninth aspect of the present invention based on the above first aspect, the noise control device further comprises: audio signal output means for outputting an audio signal to each of the plurality of sound output means; fourth signal generation means for generating a cancellation signal for canceling the audio signal outputted from the audio signal output means; and an adder for adding a signal, which is based on a sound detected by one of the first noise detection means, to the cancellation signal generated by the fourth signal generation means, and outputting the added signal to the first signal generation means. The signal based on the sound detected by one of the first noise detection means contains a signal which is based on the noise arriving in a space in which said one of the first noise detection means is provided, and contains the audio signal outputted from the audio signal output means via the sound output means provided in a same space as that of said one of the first noise detection means.

A tenth aspect of the present invention is an integrated circuit for reducing noises respectively arriving in a plurality of spaces which are acoustically independent from each other. The integrated circuit comprises: an input terminal to which an output from one of noise detection means is inputted, which noise detection means is provided in at least one of the plurality of spaces and detects a noise arriving in the at least one of the plurality of spaces in which the noise detection means is provided; signal generation means which is a single means for generating, based on the output from said one of the noise detection means which is inputted to the input terminal, a cancellation signal for canceling the noise detected by said one of the noise detection means; and an output terminal for outputting the cancellation signal, which is generated by the signal generation means, to each of sound output means which are respectively provided in the plurality of spaces so as to respectively correspond to the plurality of spaces and each of which outputs a sound to a corresponding space.

An eleventh aspect of the present invention is a headphone apparatus for reducing noises respectively arriving in two spaces which are acoustically independent from each other and which are respectively formed near left and right ears of a user. The headphone apparatus comprises: left ear sound output means, which is provided at a space formed near the left ear, for outputting a sound in the space; right ear sound output means, which is provided at a space formed near the right ear, for outputting a sound in the space; noise detection means, which is provided in at least one of the two spaces, for detecting a noise arriving in the at least one of the two spaces; and signal generation means which is a single means for generating, based on the noise detected by one of the noise detection means, a cancellation signal for canceling the noise, and outputting the generated cancellation signal to the left ear sound output means and to the right ear sound output means.

Effect of the Invention

According to the above first aspect, a noise reduction control is performed for the plurality of spaces which are acoustically independent from each other, by using a common cancellation signal generated by the single first signal generation means. In other words, according to this aspect, the single first signal generation means is used in common for the plurality of acoustically independent spaces. Here, the noises respectively arriving in the plurality of acoustically independent spaces are highly correlated to each other in a low frequency band. For this reason, when the single first signal generation means is used in common for the plurality of acoustically independent spaces, the noises respectively arriving in the plurality of acoustically independent spaces can be sufficiently reduced. As a result, according to this aspect, the number of first signal generation means each of which performs a large amount of processing can be reduced to 1, while sufficiently producing the noise reduction effect. Consequently, according to this aspect, a noise control device, which is capable of preventing an increase in an input/output delay at the first signal generation means even in the case where the processing at the first signal generation means is performed by a single arithmetic processing circuit, can be provided.

According to the above second aspect, an increase in the noise, which the user may feel due to the cancellation sound having a low correlation in other frequency bands than the low frequency band, can be avoided without newly providing a control circuit.

According to the above third aspect, the noise reduction effect can be further enhanced.

According to the above fourth aspect, since the first and second signal generation means respectively generate cancellation signals having different frequency bands from each other, processing loads on the first and second signal generation means can be reduced.

According to the above fifth aspect, an optimal control can be performed in accordance with the phase lag of the electroacoustic transfer function. This allows a frequency band, in which the noise reduction effect is obtained, to be further widened.

According to the above sixth to eighth aspects, an optimal noise reduction effect can be produced in accordance with an arrival direction of the noise.

According to the above ninth aspect, noise reduction and audio signal reproduction can be performed concurrently without affecting the audio signal.

BRIEF DESCRIPTION OF THE DRAWINGS

FIG. 10 shows a configuration of a control section 15a.

FIG. 14A shows a frequency characteristic of a detection signal $e_R$ of the right ear microphone 14b in the case where a control is performed using a detection signal $e_L$ of the left ear microphone 14a.

Figure 1:
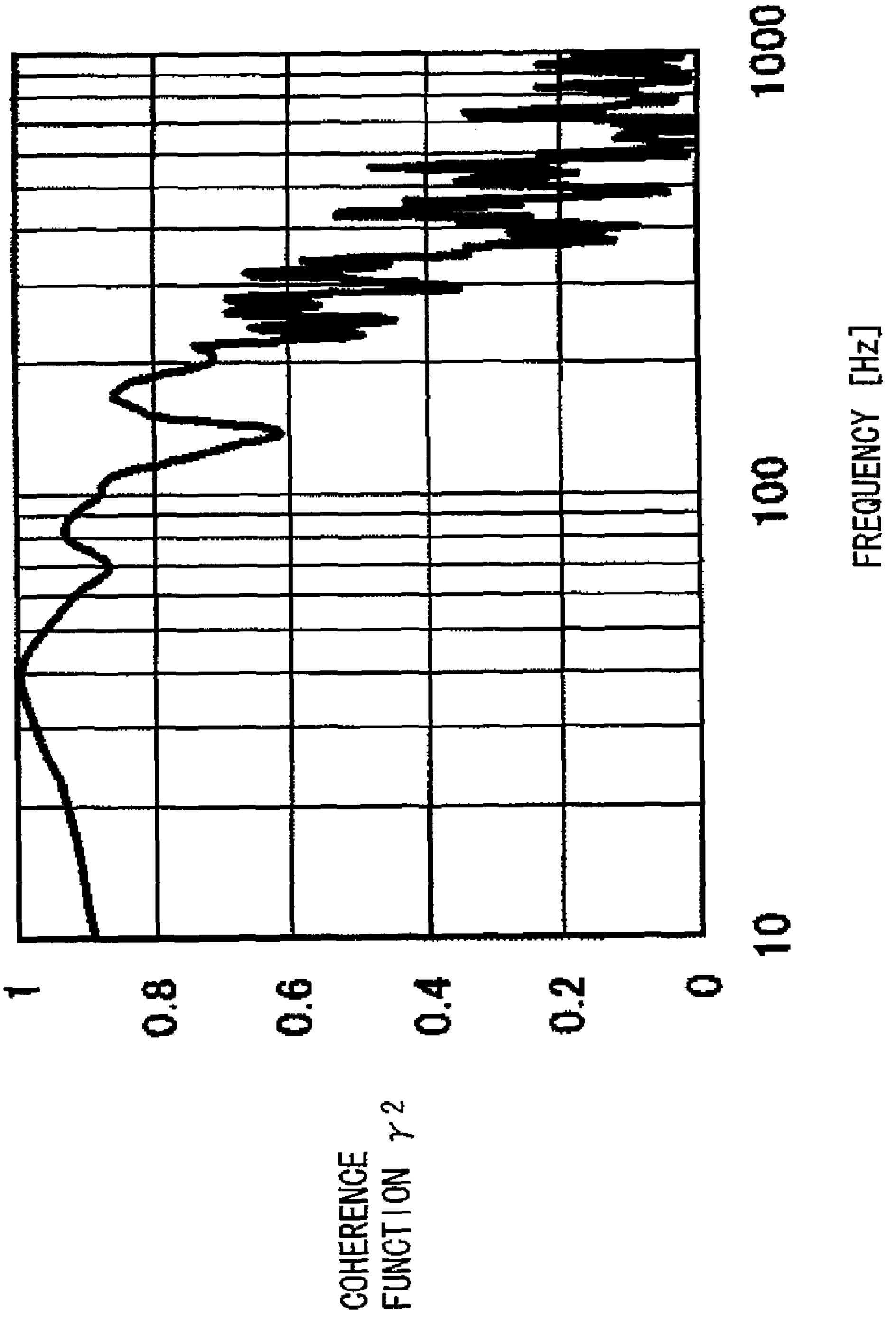
FIG. 1 shows an exemplary calculation result of a coherence function.

| DESCRIPTION OF THE REFERENCE CHARACTERS | |
|---|---|
| 11 | headband |
| 12a | left ear case |
| 12b | right ear case |
| 13a | left ear speaker |
| 13b | right ear speaker |
| 14a | left ear microphone |
| 14b | right ear microphone |
| 14c | external microphone |
| 15, 15a, 15b, 15c | control section |
| 151 | feedback control filter |
| 152 | phase inverter |
| 153 | echo canceling filter |
| 154, 20, 27, 34 | subtractor |
| 155 | filtered X filter |
| 156 | coefficient update section |
| 157 | adaptive filter |
| 158, 159 | low-pass filter |
| 16 | feedforward control section |
| 17, 21a, 21b | adder |
| 18 | audio signal output section |
| 19 | audio signal canceling section |
| 25a | left ear high frequency control section |
| 25b | right ear high frequency control section |
| 26 | echo canceling section |
| 30, 33 | switching section |
| 31 | microphone determination section |
| 32 | switching control section |

DETAILED DESCRIPTION OF THE INVENTION

Prior to describing noise control devices according to the embodiments of the present invention, a concept of the present invention will be described. In a headphone apparatus or the like, spaces which are acoustically independent from each other are formed near right and left ears of a user, respectively. For these spaces, a correlation between a noise arriving in the space formed near the left ear and a noise arriving in the space formed near the right ear is obtained using a coherence function.

The coherence function indicates a degree of correlation between the two noises. To be specific, when it is assumed that: the coherence function is $\gamma^2$ (f); a power spectrum of a noise signal $N_L$ based on the noise near the left ear is $S_{LL}$ (f); a power spectrum of a noise signal $N_R$ based on the noise near the right ear is $S_{RR}$ (f); and a cross spectrum of the noise signals $N_L$ and $N_R$ is $S_{LR}$ (f), the coherence function $\gamma^2$ (f) can be represented by an equation (3). Here, f is a frequency.

[equation 3]

$$\gamma^2(f) = \frac{|S_{LR}(f)|^2}{S_{LL}(f)S_{RR}(f)} \tag{3}$$

When the coherence function was calculated based on the equation (3), a result as shown in FIG. 1 was obtained. FIG. 1 shows an exemplary calculation result of the coherence function. The result in FIG. 1 shows that a value of the coherence function increases in accordance with a decrease in a frequency of the noises. Here, the greater the value of the coherence function, the higher is the correlation between the two noises. Thus, it is understood from the result shown in FIG. 1 that the correlation between the noise near the left ear and the noise near the right ear increases in accordance with a decrease in the frequency of the noises. Note that, the result in FIG. 1 shows that the correlation is extremely high, particularly in a low frequency band no higher than 100 Hz.

As described above, it has been discovered with respect to the acoustically independent spaces respectively formed near the left and right ears of the user that the correlation between the noise near the left ear and the noise near the right ear increases in accordance with a decrease in the frequency of the noises. This discovery means that when a cancellation signal for canceling a noise arriving in one of the spaces is used for the other space, a noise in a low frequency band can be canceled from a noise arriving in the other space. In other words, this discovery means that when a cancellation signal for canceling a noise arriving in one of the spaces is used for the other space, a noise arriving in the other space is sufficiently reduced.

Accordingly, in the present invention, for the acoustically independent spaces respectively formed near the left and right ears of the user, a cancellation signal for canceling a noise arriving in one of the spaces is used for the other space. That is, in the present invention, a control section for generating the cancellation signal is used in common for the two acoustically independent spaces. This allows the present invention to reduce, while producing a sufficient noise reduction effect, the number of control sections each of which performs a great amount of arithmetic processing. Consequently, the present invention can provide a noise control device capable of preventing an increase in an input/output delay at a control section even in the case where the processing at the control section is performed by a single arithmetic processing circuit.

First Embodiment

Figure 2:
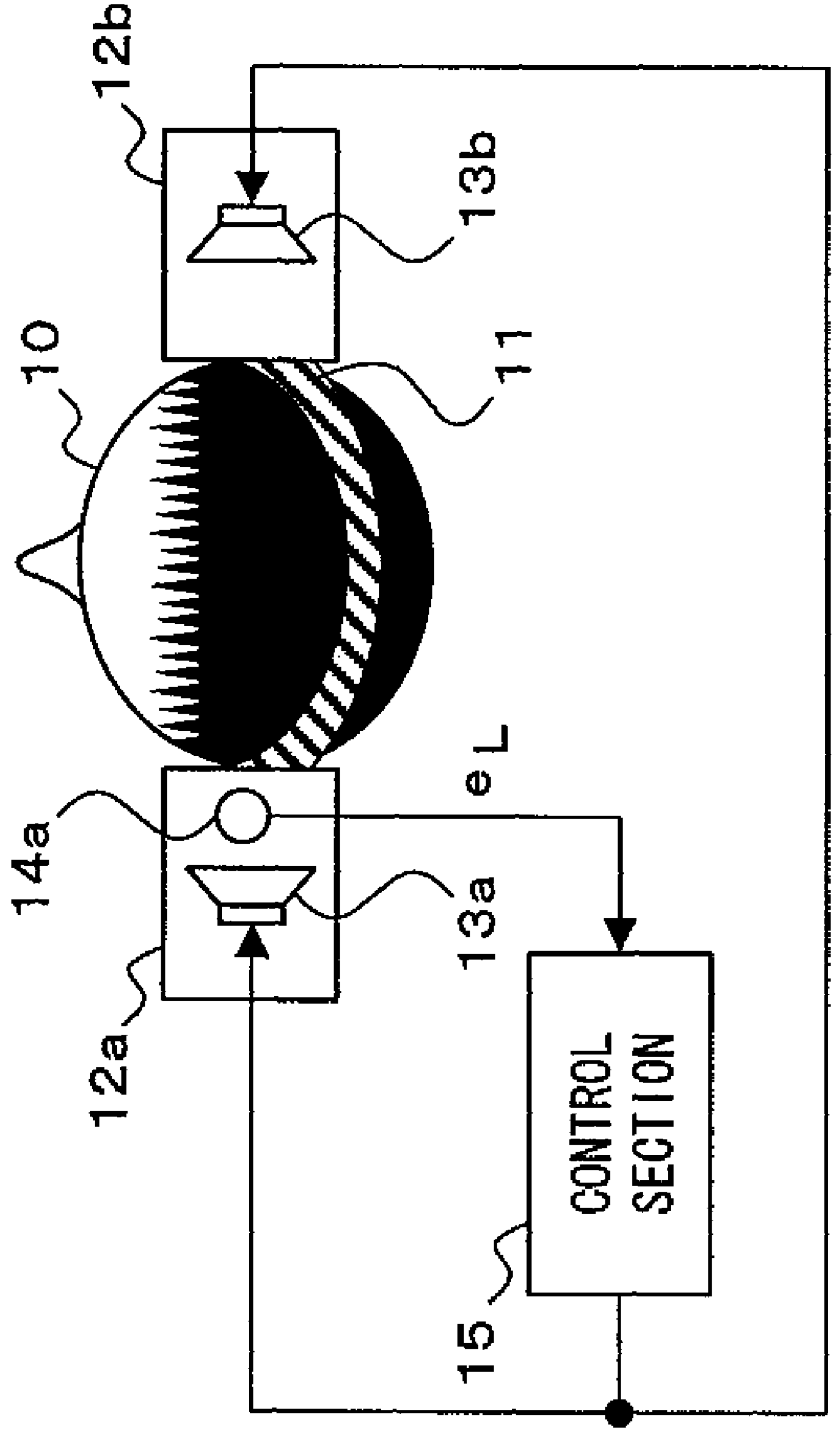
FIG. 2 shows a configuration of a noise control device according to a first embodiment.

Hereinafter, a noise control device according to a first embodiment of the present invention will be described with reference to the drawings. First, a configuration of the noise control device according to the present embodiment will be described with reference to FIG. 2. FIG. 2 shows the configuration of the noise control device according to the first embodiment. Note that, FIG. 2 shows a configuration in the case where the noise control device according to the present embodiment is applied in a headphone apparatus. FIG. 2 and later-described FIGS. 3, 7 and 8 each is a diagram which shows a view seen from above a head of a user 10 and in which the user 10 faces upward.

As shown in FIG. 2, the noise control device comprises a headband 11, a left ear case 12*a*, a right ear case 12*b*, a left ear speaker 13*a*, a right ear speaker 13*b*, a left ear microphone 14*a* and a control section 15. The left ear case 12*a* is placed near a left ear of the user 10, and the left ear case 12*a* has a space formed therein. The right ear case 12*b* is placed near a right ear of the user 10, and the right ear case 12*b* has a space formed therein. The left ear case 12*a* and the right ear case 12*b* are connected by the headband 11. The left ear speaker 13*a* is provided within the left ear case 12*a*. The right ear speaker 13*b* is provided within the right ear case 12*b*. The left ear speaker 13*a* has a same characteristic as that of the right ear speaker 13*b*. The left ear microphone 14*a* is provided within the left ear case 12*a*.

The spaces respectively formed within the left ear case 12*a* and the right ear case 12*b* are acoustically independent from each other. As described above, being acoustically independent means that an acoustic state is such that a gain of an electroacoustic transfer function between the spaces is sufficiently small. In other words, the acoustic state is such that when a sound radiated from a speaker provided in one of the spaces has arrived in the other space, a level of the sound having arrived in the other space is sufficiently small. For example, the acoustically independent spaces are, in the headphone apparatus in FIG. 2, a space formed near one ear and a space formed near the other ear. As another example, the acoustically independent spaces are spaces respectively formed in adjacent rooms separated by a wall or the like.

Next, operations of the noise control device according to the present embodiment will be described. The left ear microphone 14*a* detects a noise arriving in the left ear case 12*a*. The left ear microphone 14*a* outputs, as a detection signal $e_L$ to the control section 15, a noise signal based on the detected noise. The control section 15 generates, based on the detection signal $e_L$, a control signal for controlling a level of the detection signal $e_L$ such that the level is lowered. The control section 15 outputs the generated control signal to the left ear speaker 13*a* and to the right ear speaker 13*b*. Thus, in the noise control device according to the present embodiment, the single control section 15 is used in common for the two acoustically independent spaces.

Near the left ear, a sound based on the control signal generated by the control section 15 is outputted from the left ear speaker 13*a*. As a result, the sound based on the control signal and the noise are canceled by each other near the left ear. Thus, the control signal is a cancellation signal for canceling the noise.

In the case where the sound based on the control signal and the noise are not entirely canceled near the left ear, a control error is detected by the left ear microphone 14*a*, which control error is a residual component occurring as a result of synthesizing the sound based on the control signal and the noise. The left ear microphone 14*a* outputs, as the detection signal $e_L$ to the control section 15, an error signal based on the control error. Thus, near the left ear, the left ear microphone 14*a*, the control section 15 and the left ear speaker 13*a* form a feedback loop. The feedback loop causes the noise control device to operate such that the control error attenuates.

Near the right ear, a sound is outputted from the right ear speaker 13*b*, the sound being the same as the sound which is based on the control signal and which is outputted near the left ear. As shown in FIG. 1, a noise arriving in the right ear case 12*b* is highly correlated, in the low frequency band, to a noise arriving in the left ear case 12*a*. For this reason, near the right ear, the noise in the low frequency band which has a high correlation is canceled by the sound which is based on the control signal and which is outputted near the left ear. Thus, the control section 15 generates the cancellation signal to be used in common in the vicinity of each of the right and left ears. The control section 15 corresponds to first signal generation means of the present invention.

Further, the noise control device according to the present embodiment comprises: a microphone amplifier for amplifying the detection signal $e_L$ detected by the left ear microphone 14*a*: and a speaker amplifier for amplifying the control signal of the control section 15 so as to drive the left ear speaker 13*a* and the right ear speaker 13*b*. However, these components are omitted in FIG. 2.

Figure 3:
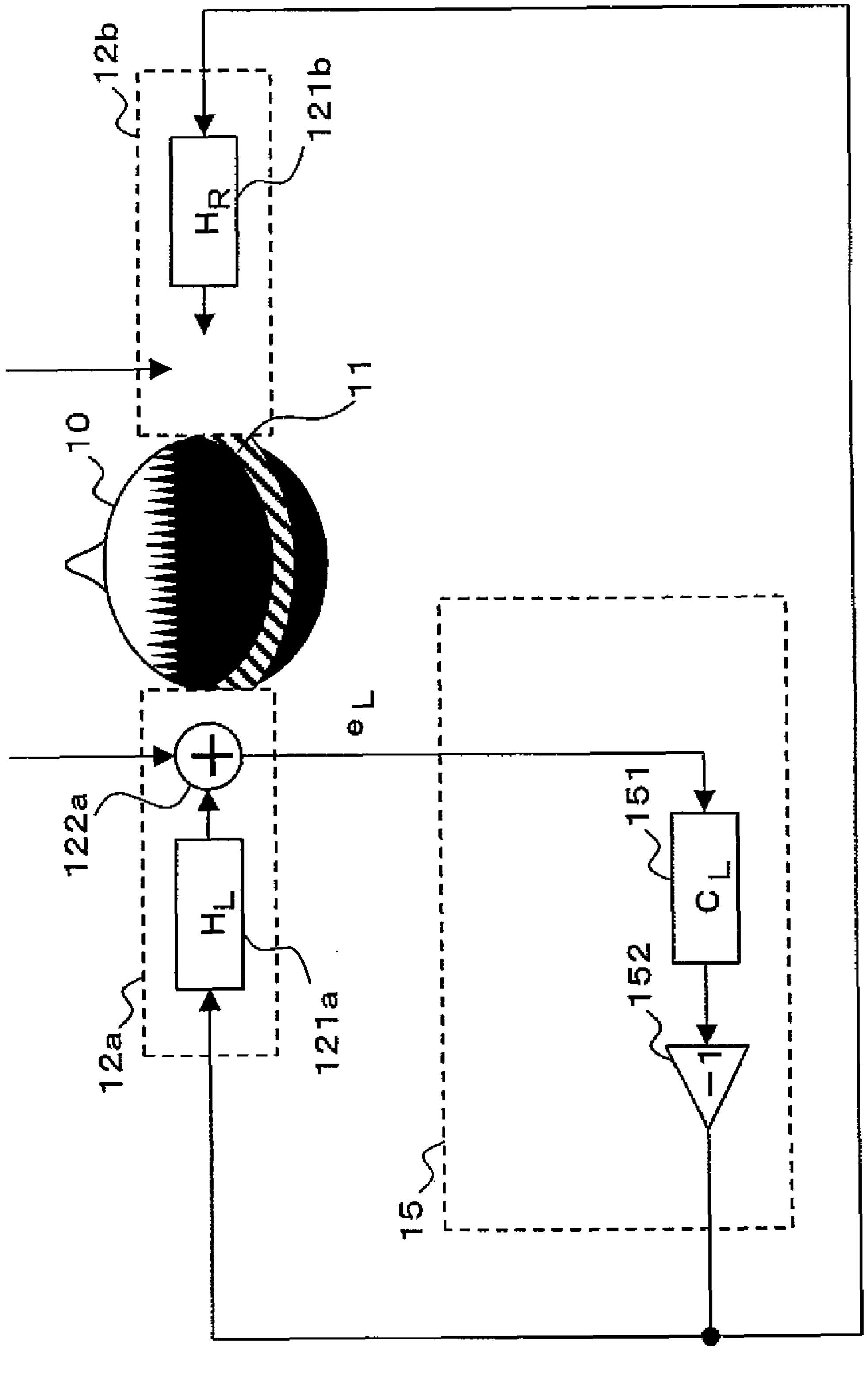
FIG. 3 shows, by blocks of signal processing, an exemplary configuration of the noise control device shown in FIG. 2.

Next, a configuration and processing of the control section 15 will be described in detail with reference to FIG. 3. FIG. 3 shows, by blocks of signal processing, an exemplary configuration of the noise control device shown in FIG. 2. It is assumed for FIG. 3 that components, which are denoted by the same reference numerals as those used for components in FIG. 2, have the same functions as those of the components in FIG. 2, and descriptions thereof will be omitted.

A block 121*a* in the left ear case 12*a* indicates an electroacoustic transfer function $H_L$ from an input of the left ear speaker 13*a* to an output of the left ear microphone 14*a*. A block 121*b* in the right ear case 12*b* indicates an electroacoustic transfer function $H_R$ from an input of the right ear speaker 13*b* to an output of a right ear microphone 14*b*. An adder 122*a* adds an output signal of the block 121_a_ to the noise signal $N_L$ indicating the noise arriving in the left ear case 12_a_. A signal outputted from the adder 122_a_ is the aforementioned detection signal $e_L$.

The control section 15 comprises a feedback control filter 151 and a phase inverter 152. For the feedback control filter 151, a filter coefficient indicating a transfer function $C_L$ is set. The detection signal $e_L$ outputted from the adder 122_a_ is inputted to the feedback control filter 151. The phase inverter 152 inverts a phase of an output signal of the feedback control filter 151. An output signal from the phase inverter 152 is inputted to the block 121_a_ and to the block 121_b_. Here, a transfer function from the noise signal $N_L$ to the detection signal $e_L$ is represented by an equation (4).

[equation 4]

$$\frac{e_L}{N_L} = \frac{1}{1 + C_L H_L} \tag{4}$$

Note that, the transfer function $C_L$ of the feedback control filter 151 is, as shown in an equation (5), set so as to have an inverse characteristic to that of the electroacoustic transfer function $H_L$ at the left ear. Here, α indicates a filter gain of a fixed frequency.

[equation 5]

$$C_L = \frac{\alpha}{H_L} \tag{5}$$

Here, as is clear from the equation (1), when a noise arrives in the left ear case 12_a_, the left ear microphone 14_a_ outputs $N_L/(1+C_L \times H_L)$ as the detection signal $e_L$. The detection signal $e_L$ is inputted to the feedback control filter 151. At this point, the control signal generated at the feedback control filter 151 is $C_L \times N_L/(1+C_L \times H_L)$. Since the transfer function $C_L$ is set as shown in the equation (5), the control signal is $N_L(H_L \times (1+1/\alpha))$. The control signal is inputted to the block 121_a_ after a phase of the control signal is inverted by the phase inverter 152. Accordingly, a cancellation sound radiated from the left ear speaker 13_a_ to the vicinity of the left ear is $-H_L \times N_L/(H_L \times (1+1/\alpha)) = -N_L/(1+1/\alpha)$. As a result, the greater the filter gain α, the nearer to $-N_L$ the cancellation sound becomes, whereby the noise arriving near the left ear is canceled.

On the other hand, a cancellation sound radiated from the right ear speaker 13_b_ to the vicinity of the right ear is $-H_R \times N_L/(H_L \times (1+1/\alpha))$. Here, the left ear speaker 13_a_ and the right ear speaker 13_b_ have a same characteristic. That is, a relationship $H_L \approx H_R$ is realized. Also, as shown in FIG. 1, a relational equation $N_L \approx N_R$ is realized for the noise in the low frequency band. Further, when it is assumed that the filter gain α is large and a relational equation $1/\alpha \approx 0$ is realized, an equation (6) is realized for the noise in the low frequency band. As a result, the noise in the low frequency band is canceled near the right ear.

[equation 6]

$$N_R + \left(H_R \frac{-N_L}{H_L(1 + 1/\alpha)}\right) \cong N_R - N_L \cong 0 \tag{6}$$

As described above, the noise control device according to the present embodiment performs a control so as to reduce the noises for the two acoustically independent spaces, by using the common control signal generated by the single control section 15. In other words, the noise control device according to the present embodiment uses the control section 15 for common use between the two acoustically independent spaces. Here, the noises respectively arriving in the two acoustically independent spaces are highly correlated to each other in the low frequency band as shown in FIG. 1. For this reason, the noise arriving in the left ear case 12_a_ can be canceled for all the frequency bands, and the noise arriving in the right ear case 12_b_ can be canceled for the low frequency band. In other words, even if the control section 15 is used in common for the two acoustically independent spaces, the noises respectively arriving in the two acoustically independent spaces can be reduced sufficiently. Thus, the noise control device according to the present embodiment can reduce, while sufficiently producing the noise reduction effect, the number of control sections 15 each of which performs a large amount of arithmetic processing. Consequently, according to the present embodiment, the noise control device, which is capable of preventing an input/output delay at the control section 15 from increasing even in the case where the processing at the control section 15 is performed by a single arithmetic processing circuit, can be provided.

Further, the noise control device according to the present embodiment performs a control for the two acoustically independent spaces. Therefore, in the noise control device according to the present embodiment, there is no necessity to take into account a leak of the cancellation sound (crosstalk) from the right ear speaker 13_b_ to the left ear microphone 14_a_. Accordingly, the noise control device according to the present embodiment provides an advantage that there is no necessity to provide a circuit for controlling the leak of the cancellation sound.

In the processing at the control section 15 illustrated in FIG. 3, the sound outputted near the right ear is the same as the sound which is based on the control signal and which is outputted near the left ear. Thus, a cancellation sound, which has a low correlation and which is in a frequency band different from the low frequency band, is outputted near the right ear. Here, in the case where the cancellation sound, which is in a frequency band in which the correlation thereof is low, is outputted near the right ear, there may be a case where the cancellation sound does not have a same amplitude as and is not in antiphase to the noise arriving in the right ear case 12_b_, since the cancellation sound has a high frequency. In the case where the cancellation sound does not have a same amplitude as and is not antiphase to the noise arriving in the right ear case 12_b_, the cancellation sound is, in the frequency band thereof, superimposed on the noise, and the noise is increased accordingly. In other words, the user 10 feels that the noise has increased in this frequency band. In this case, it is preferred to cause the control section 15 to generate a control signal whose characteristic corresponds to a frequency characteristic of the coherence function shown in FIG. 1. Since, in this case, a frequency characteristic of the cancellation sound corresponds to the frequency characteristic of the coherence function, the increase in the noise which the user 10 feels can be avoided without newly providing a control circuit.

Note that, the characteristic of the control signal, which corresponds to the frequency characteristic of the coherence function, is such that a level of the control signal increases in accordance with a decrease in a frequency of the control signal. This characteristic may, e.g., simulate the frequency characteristic of the coherence function, or may be such that in the case where a predetermined frequency is set as a reference frequency, the level of the control signal is at a fixed value when the frequency of the control signal is no higher than the reference frequency, and the level of the control signal decreases from the fixed value in accordance with an increase in the frequency of the control signal from the reference frequency.

Figure 4A:
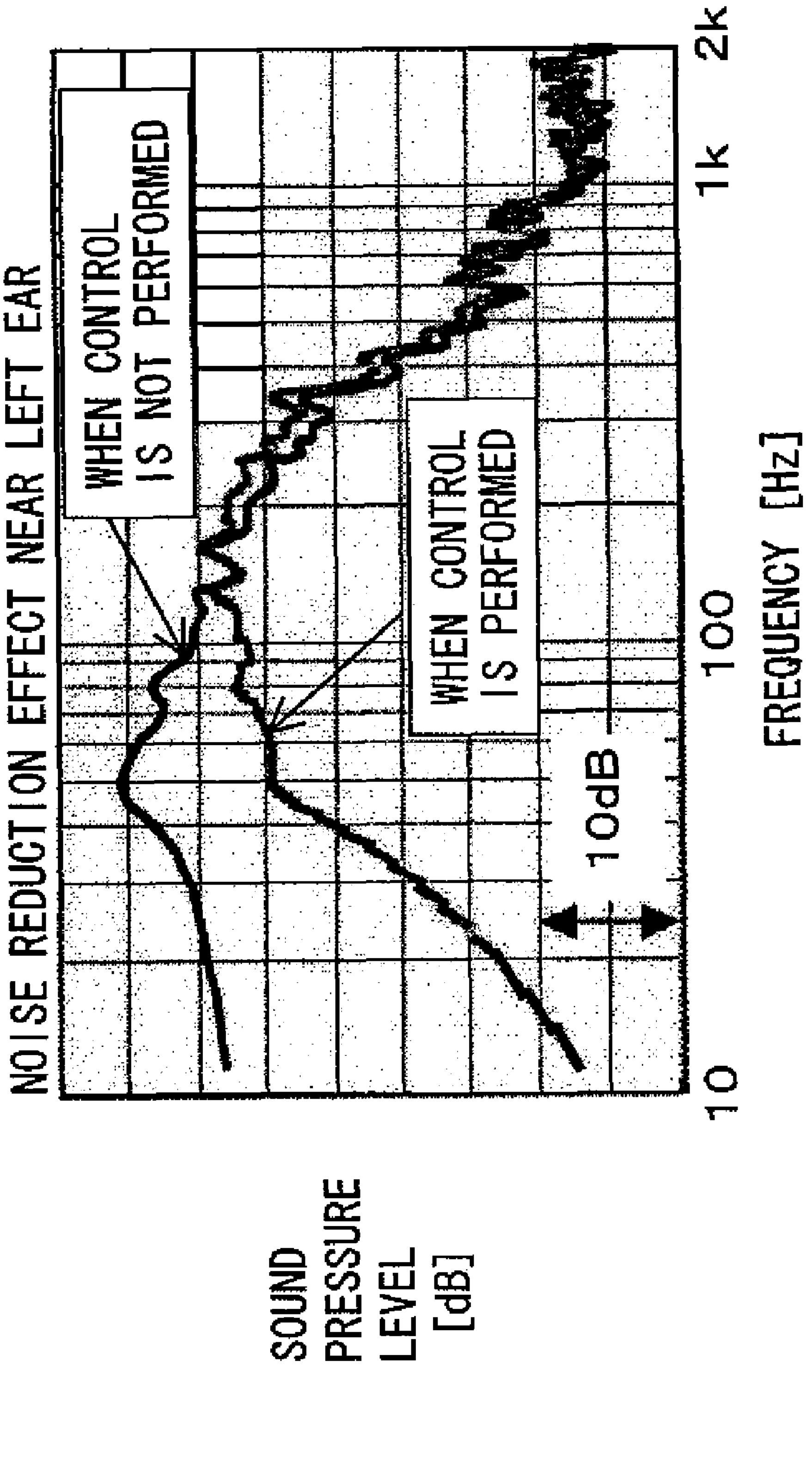
FIG. 4A shows a noise reduction effect near a left ear.
Figure 4B:
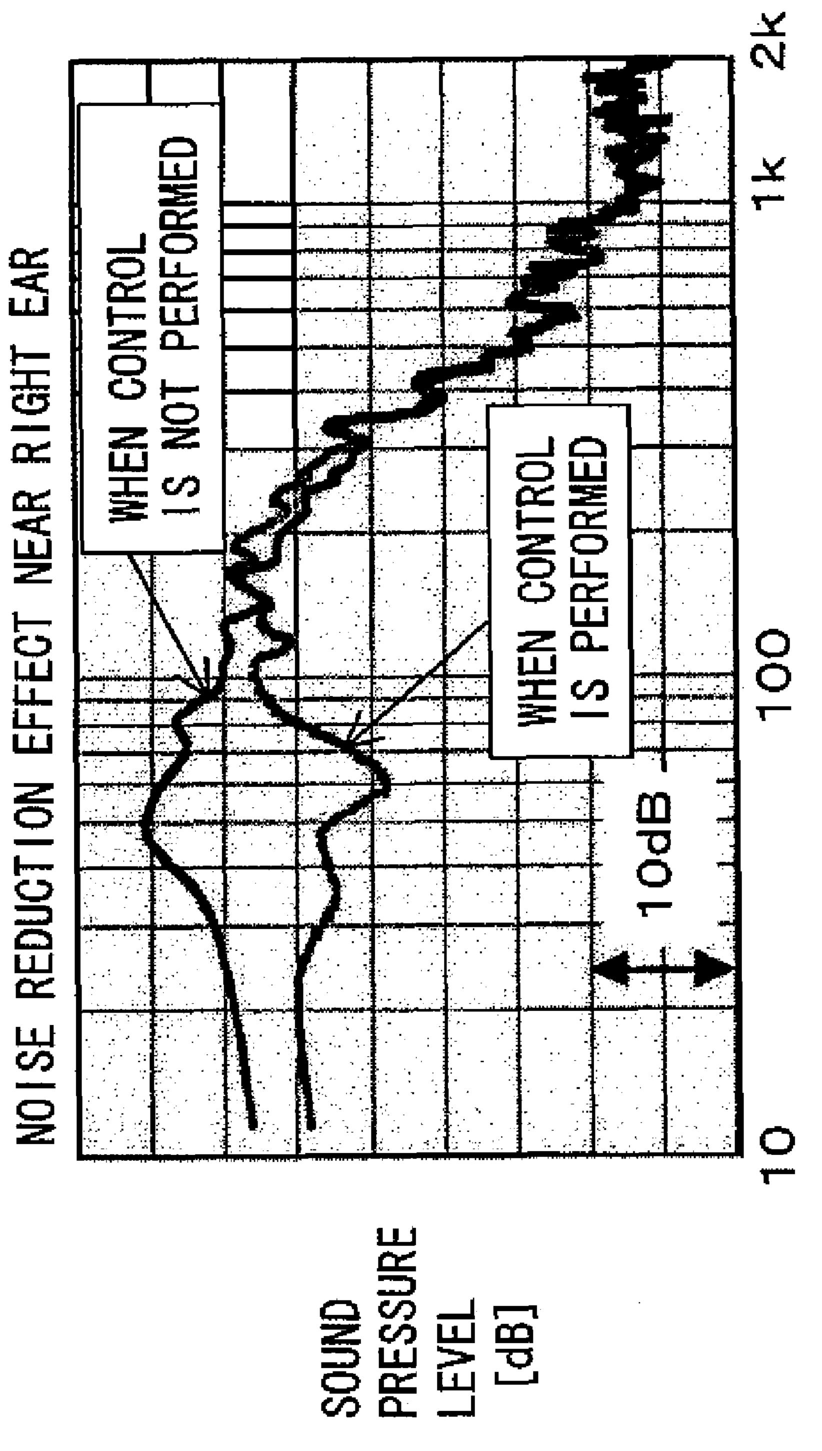
FIG. 4B shows a noise reduction effect near a right ear.

FIGS. 4A and B show noise reduction effects in the case where the control section 15 generates a control signal having the characteristic corresponding to the frequency characteristic of the coherence function. In FIGS. 4A and B, a reference frequency is set to 150 Hz, and the control signal used herein has a characteristic such that the level of the control signal is at a fixed value when the frequency thereof is no higher than 150 Hz, and the level of the control signal decreases from the fixed value in accordance with an increase in the frequency thereof from 150 Hz. FIG. 4A shows a noise reduction effect near the left ear. FIG. 4B shows a noise reduction effect near the right ear. As shown in FIG. 4A, near the left ear, a level of the noise in a low frequency band no higher than 150 Hz is sufficiently reduced when a control is performed, as compared to when the control is not performed. Also as shown in FIG. 4B, near the right ear, a level of the noise in the frequency band no higher than 150 Hz is reduced when the control is performed as compared to when the control is not performed. Although the amount of the reduced level near the right ear is smaller than that near the left ear, it is clearly understood that the sufficient noise reduction effect, which is no smaller than 10 db, is obtained.

Figure 5:
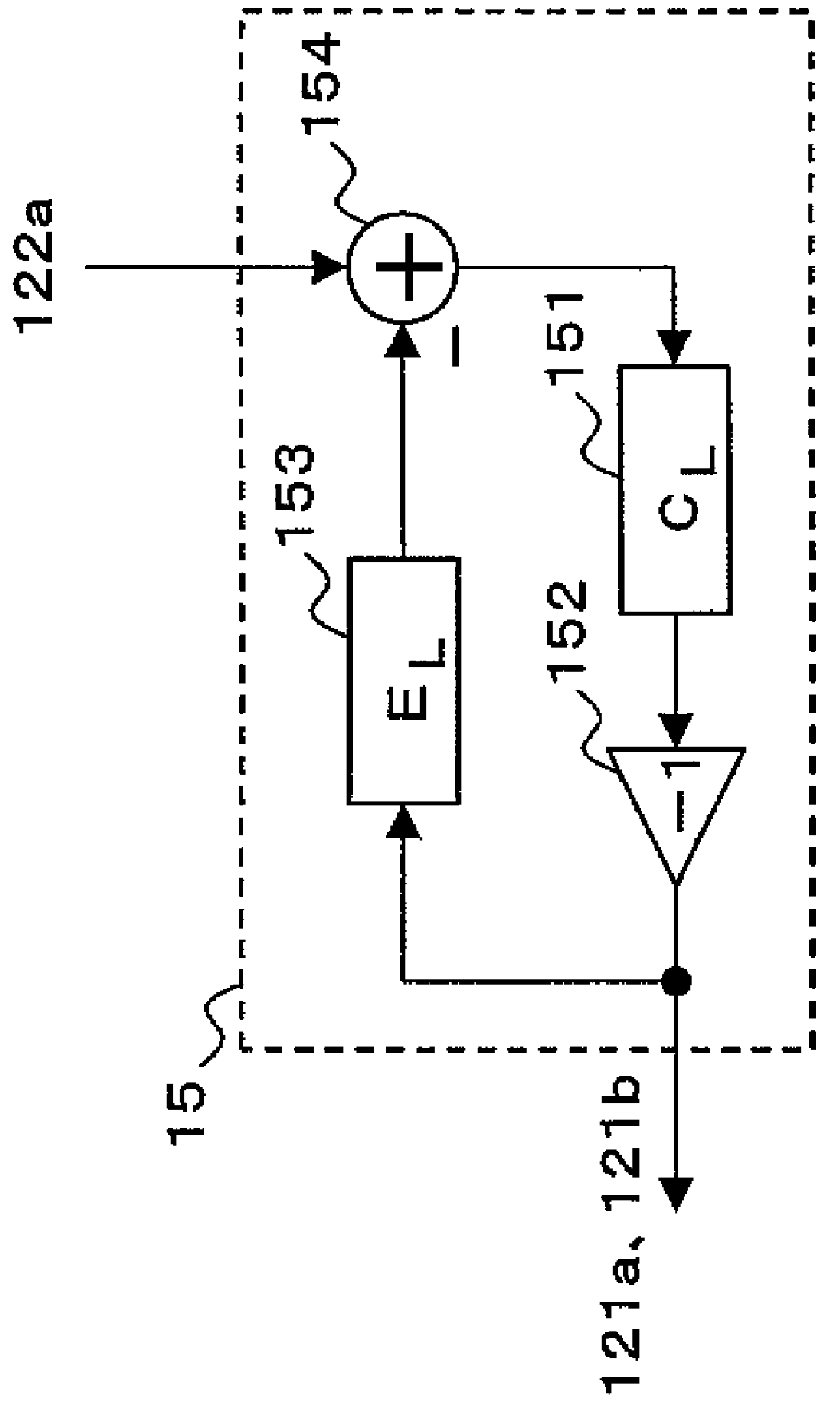
FIG. 5 shows another exemplary configuration of a control section 15 shown in FIG. 3.

Still further, the configuration of the above-described control section 15 is not limited to the configuration shown in FIG. 3. The control section 15 may further comprise, as shown in FIG. 5, an echo cancellation filter 153 and a subtractor 154. FIG. 5 shows another exemplary configuration of the control section 15 shown in FIG. 3. The echo cancellation filter 153 is a filter for canceling echo which contributes to howling. For the echo cancellation filter 153, a filter coefficient indicating a transfer function $E_L$ is set. The subtractor 154 subtracts an output signal of the echo cancellation filter 153 from the detection signal $e_L$ outputted from the adder 122*a*. An output signal from the subtractor 154 is inputted to the feedback control filter 151. An output signal from the phase inverter 152 is inputted to the echo cancellation filter 153 and the blocks 121*a* and 121*b*. Here, a transfer function from the noise signal $N_L$ to the detection signal $e_L$ is represented by an equation (7).

[equation 7]

$$\frac{e_L}{N_L} = \frac{1 - C_L E_L}{1 + C_L (H_L - E_L)} \tag{7}$$

Here, the transfer function $E_L$ of the echo cancellation filter 153 is set so as to simulate the electroacoustic transfer function $H_L$ at the left ear. In this case, the denominator of the equation (7) is 1, and the control section 15 always operates stably. Further, the transfer function $C_L$ of the feedback control filter 151 is set, as shown in the equation (5), so as to have an inverse characteristic to that of the electroacoustic transfer function $H_L$ at the left ear. In this case, the right-hand side of the equation (7) is 0, and the noise near the left ear is canceled. Thus, when the control section 15 has the configuration shown in FIG. 5, the feedback loop is stabilized. Consequently, an occurrence of an unusual sound due to oscillation, such as howling, can be suppressed.

Figure 6:
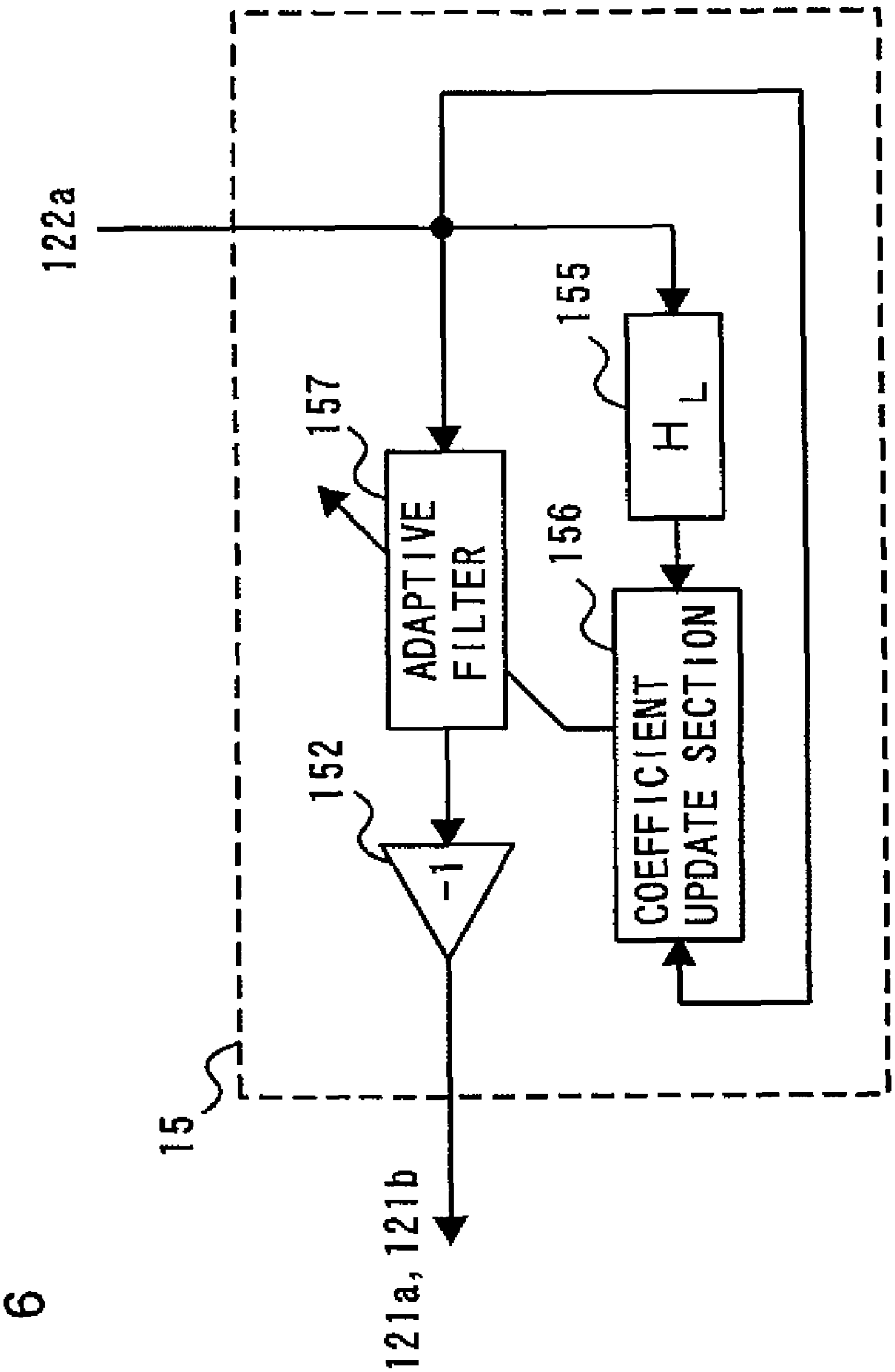
FIG. 6 shows another exemplary configuration of the control section 15 shown in FIG. 3.

Still further, the above-described control section 15 may have a structure shown in FIG. 6. FIG. 6 shows another exemplary configuration of the control section 15 shown in FIG. 3. In FIG. 6, the control section 15 comprises a filtered X filter 155, a coefficient update section 156, an adaptive filter 157 and the phase inverter 152. The filtered X filter 155 is a filter for which a filter coefficient simulating the electroacoustic transfer function $H_L$ is set. The coefficient update section 156 sequentially calculates a filter coefficient based on the LMS algorithm, thereby updating a filter coefficient to be set for the adaptive filter 157. The adaptive filter 157 is a filter for which the set filter coefficient can be sequentially updated. It is assumed here that each component of the control section 15 shown in FIG. 6 is structured by a digital circuit. In the case where each component of the control section 15 is structured by a digital circuit, the control section 15 comprises, although not shown in FIG. 6, an analogue/digital converter, a digital/analogue converter, an anti-aliasing filter and the like.

The coefficient update section 156 sequentially calculates, based on an update equation shown as an equation (8), the filter coefficient such that a level of the detection signal $e_L$ outputted from the adder 122*a* is lowered.

[equation 8]

$$w(k+1) = w(k) + 2\mu e_L(k) \times (k) \tag{8}$$

Here, w(k) is a filter coefficient vector at a sampling time k; μ is an adaptive step size; $e_L(k)$ is the detection signal at the sampling time k; and x(k) is an input vector at the sampling time k. Also, x(k) is a result of converting an output signal of the filtered X filter 155 into a vector from a sampling time k−m+1 to the sampling time k (m is the number of filter taps of the adaptive filter 157). The filter coefficient calculated by the coefficient update section 156 is set as a filter coefficient for the adaptive filter 157. The coefficient update section 156 terminates the calculation at a point when the detection signal $e_L$ has become small and converged. By using the filter coefficient which is set for the adaptive filter 157 at this termination point, the noises near both the right and left ears can be reduced, similarly to the processing illustrated in FIG. 3. Note that, the echo cancellation filter 153 and the subtractor 154 shown in FIG. 5 may be further added to the configuration shown in FIG. 6.

Although, in the noise control device shown in FIG. 2, the left ear microphone 14*a* for detecting a noise is provided within the left ear case 12*a*, the present invention is not limited thereto. Such a microphone for detecting a noise may be provided not within the left ear case 12*a* but within the right ear case 12*b*. In this case, the filter coefficient for the feedback control filter 151, which is a component of the control section 15 shown in FIG. 3, is set so as to have an inverse characteristic to that of the electroacoustic transfer function $H_R$ at the right ear.

Further, the noise control device shown in FIG. 2 is applied in a headphone apparatus. However, the present invention is not limited thereto. The noise control device according to the present embodiment may be applied in any device as long as there is a necessity in said any device to reduce noises arriving in acoustically independent spaces.

Still further, in the noise control device shown in FIG. 2, the two spaces within the left ear case 12*a* and the right ear case 12*b* are assumed to be the acoustically independent spaces. However, the number of spaces is not limited to 2. There may be three or more acoustically independent spaces. In such a case, the spaces are each provided with a speaker; at least one of the spaces is provided with a microphone; and only one control section 15 is provided. The control section 15 generates a control signal for canceling a noise detected by the microphone, and outputs a common control signal to the speaker provided in each space.

Figure 7:
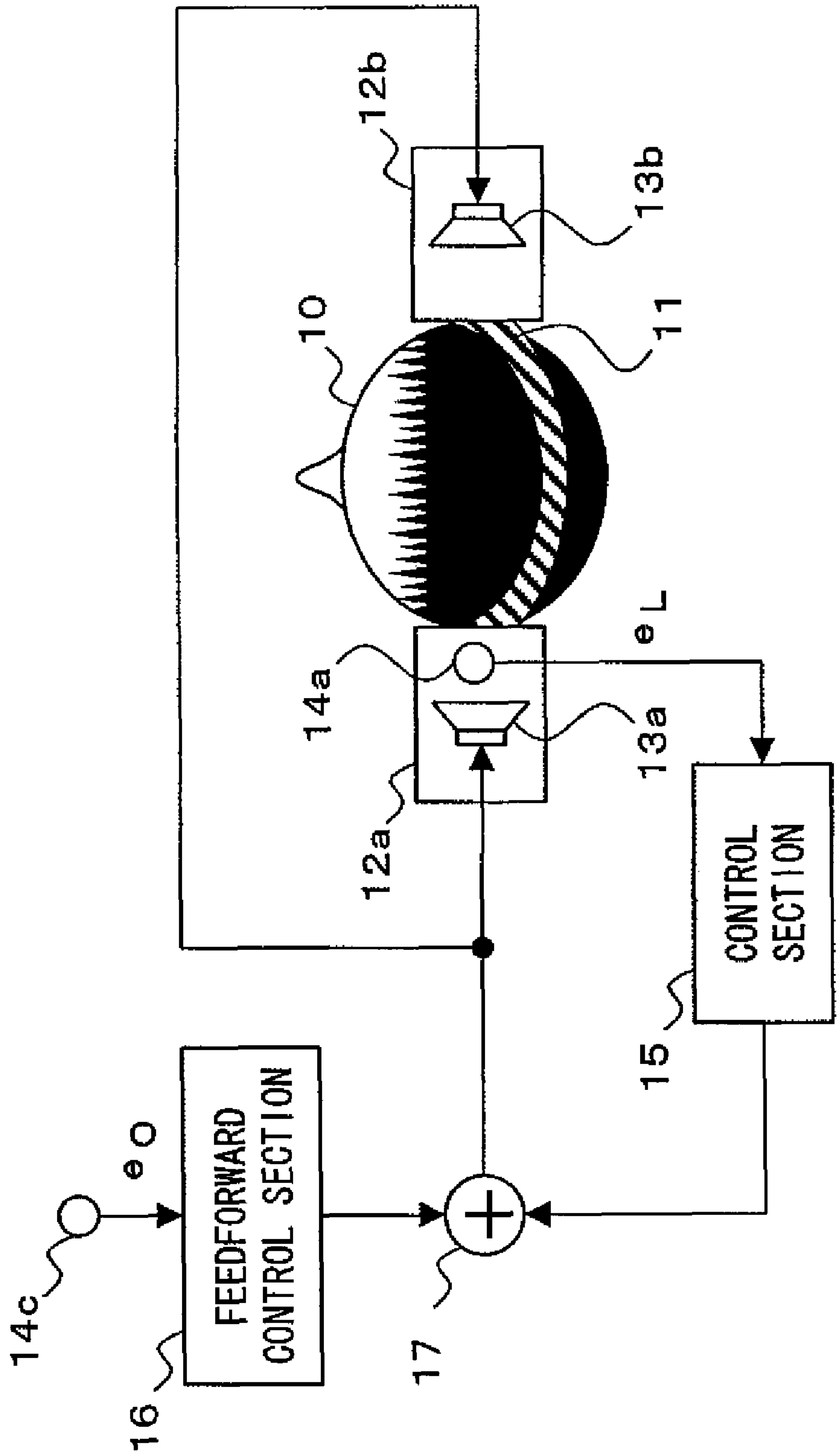
FIG. 7 shows a configuration in which the noise control device shown in FIG. 2 further comprises an external microphone 14c, a feedforward control section 16 and an adder 17.

Still further, in the noise control device shown in FIG. 2, the noise canceling control is performed only by the feedback control using the detection signal $e_L$ of the left ear microphone 14*a* provided within the left ear case 12*a*. However, the noise control device shown in FIG. 2 may further comprise, as shown in FIG. 7, an external microphone 14*c*, a feedforward control section 16 and an adder 17. FIG. 7 shows a configuration in which the noise control device shown in FIG. 2 further comprises the external microphone 14*c*, the feedforward control section 16 and the adder 17.

The external microphone 14*c* is provided outside the left ear case 12*a*. An external space of the left ear case 12*a* is not acoustically independent but has a noise source. The external microphone 14*c* detects a noise which is present outside the left ear case 12*a*. In other words, the external microphone 14*c* detects a noise arriving from the noise source. The external microphone 14*c* outputs an external noise signal, which is based on the detected external noise, as an external detection signal $e_o$ to the feedforward control section 16. Based on a filter coefficient indicating a transfer function G which has been set, the feedforward control section 16 generates, as a control signal, a cancellation signal for canceling the external detection signal $e_o$. Thus, the feedforward control section 16 generates the cancellation signal for canceling the external noise. The feedforward control section 16 corresponds to second signal generation means of the present invention.

The transfer function G of the feedforward control section 16 may be set such that an equation (9) is satisfied when an electroacoustic transfer function from a position of the external microphone 14*c* to a position of the left ear microphone 14*a* is H. Note that, $H_L$ in the equation (9) is an electroacoustic transfer function from an input of the left ear speaker 13*a* to an output of the left ear microphone 14*a*.

[equation 9]

$$H+H_LG=0 \tag{9}$$

As is clear from the equation (9), the transfer function G of the feedforward control section 16 is set such that $G=-H/H_L$. By having this configuration, a noise reduction effect by feedforward control is further obtained in addition to the noise reduction effect by the feedback control. Consequently, a further enhanced noise reduction effect is obtained.

Figure 8:
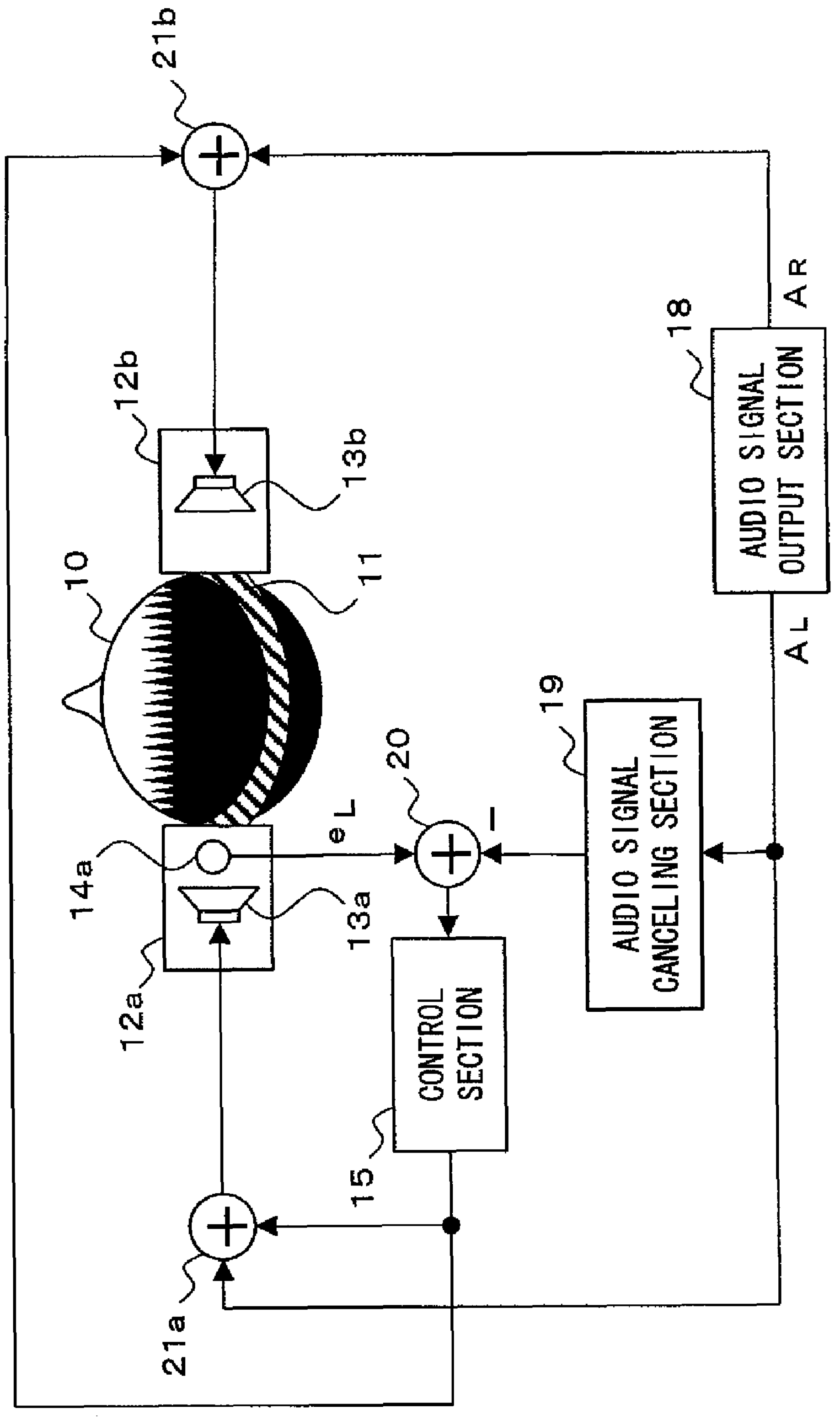
FIG. 8 shows a configuration in which a noise reduction function and an audio signal outputting function are combined.

Although the noise control device shown in FIG. 2 has a configuration which has only a noise reduction function, the control device may have a configuration in which the noise reduction function and an audio signal outputting function are combined. FIG. 8 shows the configuration in which the noise reduction function and the audio signal outputting function are combined. It is assumed for FIG. 8 that components, which are denoted by the same reference numerals as those used for components in FIG. 2, have the same functions as those of the components in FIG. 2, and descriptions thereof will be omitted.

The configuration shown in FIG. 8 is a result of adding, to the configuration shown in FIG. 2, an audio signal output section 18, an audio signal canceling section 19, a subtractor 20 and adders 21*a* and 21*b*. The audio signal output section 18 outputs stereo audio signals such as music. As shown in FIG. 8, the audio signal output section 18 outputs an audio signal $A_L$ to the left ear and an audio signal $A_R$ to the right ear. The audio signal canceling section 19 generates, based on a filter coefficient indicating a transfer function simulating the electroacoustic transfer function $H_L$, a cancellation signal for canceling the audio signal $A_L$. Thus, the audio signal canceling section 19 generates the cancellation signal for canceling the audio signal $A_L$. The audio signal canceling section 19 corresponds to fourth signal generation means of the present invention. The subtractor 20 subtracts, from the detection signal $e_L$, the cancellation signal for canceling the audio signal $A_L$. An output signal of the subtractor 20 is inputted to the control section 15. A control signal outputted from the control section 15 is added by the adder 21*a* to the audio signal $A_L$. An output signal from the adder 21*a* is inputted to the left ear speaker 13*a*. The left ear speaker 13*a* outputs a sound based on the control signal and the audio signal $A_L$. Similarly, the control signal outputted from the control section 15 is added by the adder 21*b* to the audio signal $A_R$. An output signal from the adder 21*b* is inputted to the right ear speaker 13*b*. The right ear speaker 13*b* outputs a sound based on the control signal and the audio signal $A_R$.

Here, the detection signal $e_L$ from the left ear microphone 14*a* contains the audio signal $A_L$. However, the subtractor 20 subtracts, from the detection signal $e_L$, the cancellation signal for canceling the audio signal $A_L$. Consequently, the audio signal $A_L$ is not inputted to the control section 15, and the same processing as that illustrated in FIG. 3 is performed by the control section 15.

As described above, according to the configuration shown in FIG. 8, noise reduction and stereo audio signal reproduction can be performed concurrently. Further, according to the configuration shown in FIG. 8, noises respectively arriving near both the ears can be reduced without affecting audio signals. Note that, the audio signal output section 18 may output not only stereo audio signals but also monaural signals to both the ears. Further, the audio signal output section 18 may downmix multichannel audio signals, e.g., DVD contents, and output resultant signals to both the ears.

Second Embodiment

Hereinafter, a noise control device according to a second embodiment of the present invention will be described with reference to the drawings. Usually, in a high frequency band, a phase lag of each of the aforementioned electroacoustic transfer functions $H_L$ and $H_R$ occurs. Accordingly, there is a case where even if the transfer function $C_L$ of the control section 15 described in the first embodiment is set so as to have the inverse characteristic to that of the electroacoustic transfer function $H_L$, the transfer function $C_L$ does not have the inverse characteristic in a high frequency band, whereby the noise reduction effect decreases. For this reason, in the present invention, for a frequency band which is higher than a predetermined frequency and in which a phase lag of the electroacoustic transfer function occurs, a control is separately performed by using a high frequency control section for which a filter coefficient based on the electroacoustic transfer function having the phase lag is set.

Figure 9:
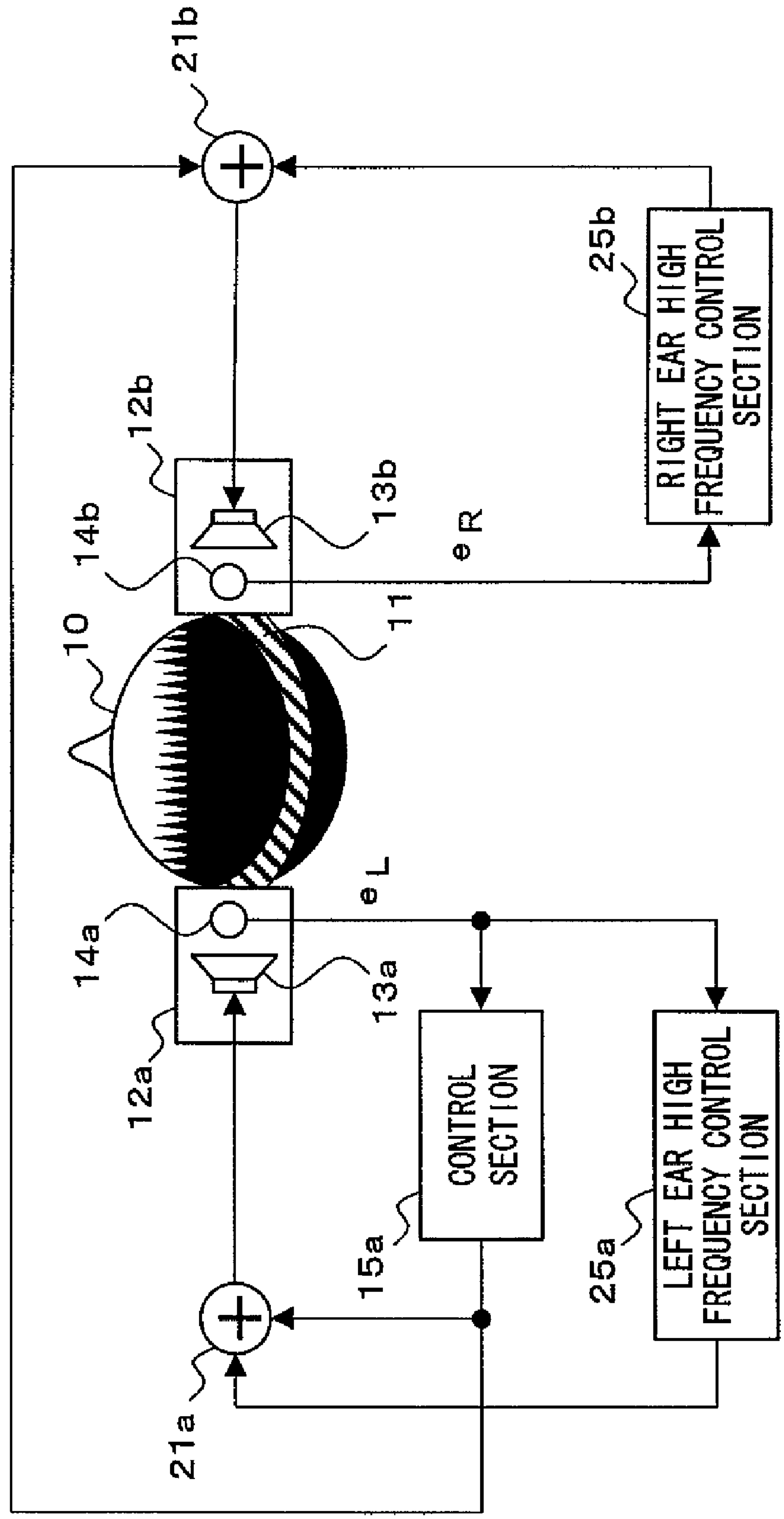
FIG. 9 shows a configuration of a noise control device according to a second embodiment.

Hereinafter, the noise control device according to the second embodiment will be described with reference to FIG. 9. FIG. 9 shows a configuration of the noise control device according to the second embodiment. It is assumed for FIG. 9 that components, which are denoted by the same reference numerals as those used for components of the noise control device according to the first embodiment shown in FIG. 2, have the same functions as those of the components of the noise control device shown in FIG. 2, and detailed descriptions thereof will be omitted. Note that, FIG. 9 and later-described FIG. 11 each are a diagram which shows a view seen from above a head of the user 10 and in which the user 10 faces upward.

As shown in FIG. 9, the noise control device comprises the headband 11, the left ear case 12*a*, the right ear case 12*b*, the left ear speaker 13*a*, the right ear speaker 13*b*, the left ear microphone 14*a*, the right ear microphone 14*b*, a control section 15*a*, the adders 21*a* and 21*b*, a left ear high frequency control section 25*a*, and a right ear high frequency control section 25*b*. The configuration shown in FIG. 9 is different from the first embodiment shown in FIG. 2 in that the configuration shown in FIG. 9 newly comprises the right ear microphone 14*b*, the adders 21*a* and 21*b*, the left ear high frequency control section 25*a*, and the right ear high frequency control section 25*b*, and also, the control section 15 according to the first embodiment shown in FIG. 2 is replaced with the control section 15*a*. In this configuration, the right ear microphone 14*b* is provided within the right ear case 12*b*, and detects a noise arriving in a space formed near the right ear of the user 10.

Next, operations of the noise control device according to the present embodiment will be described. The left ear microphone 14*a* detects a noise arriving in the left ear case 12*a*. The left ear microphone 14*a* outputs a noise signal, which is based on the detected noise, as the detection signal $e_L$ to the control section 15*a* and to the left ear high frequency control section 25*a*. The control section 15*a* generates, based on the detection signal $e_L$, a control signal for controlling a level of the detection signal $e_L$ such that the level is lowered, the control signal having a frequency no higher than a predetermined frequency. In other words, the control section 15*a* generates a cancellation signal for canceling a noise arriving in the left ear case 12*a*, the noise having the frequency no higher than the predetermined frequency. Here, the predetermined frequency is lower than a frequency at which a phase lag of the electroacoustic transfer function $H_L$ occurs. The control section 15*a* outputs the generated control signal to the adders 21*a* and 21*b*. The left ear high frequency control section 25*a* generates, based on the detection signal $e_L$, a control signal for controlling a level of the detection signal $e_L$ such that the level is lowered, the control signal having a higher frequency than the predetermined frequency. In other words, the left ear high frequency control section 25*a* generates a cancellation signal for canceling a noise arriving in the left ear case 12*a*, the noise having the higher frequency than the predetermined frequency. The left ear high frequency control section 25*a* outputs the generated control signal to the adder 21*a*. The adder 21*a* adds the control signal generated by the control section 15*a* to the control signal generated by the left ear high frequency control section 25*a*. A signal resulting from the addition at the adder 21*a* is inputted to the left ear speaker 13*a*. The left ear speaker 13*a* outputs sounds based on the control signals generated by the control section 15*a* and the left ear high frequency control section 25*a*. As a result, the sounds, which are based on the control signals, and the noises are canceled by each other near the left ear.

In the case where the sounds, which are based on the control signals, and the noises are not entirely canceled near the left ear, a control error is detected by the left ear microphone 14*a*, which control error is a residual component occurring as a result of synthesizing the sounds, which are based on the control signals, and the noises. The left ear microphone 14*a* outputs an error signal, which is based on the control error, as the detection signal $e_L$ to the control section 15*a* and to the left ear high frequency control section 25*a*. Thus, the left ear microphone 14*a*, the control section 15*a*, the adder 21*a* and the left ear speaker 13*a* form a feedback loop near the left ear. Further, another feedback loop is formed near the left ear by the left ear microphone 14*a*, the left ear high frequency control section 25*a*, the adder 21*a* and the left ear speaker 13*a*. These two feedback loops cause the noise control device to operate in such a manner that the control error near the left ear further attenuates as compared to the first embodiment.

Near the right ear, the right ear microphone 14*b* detects a noise arriving in the right ear case 12*b*. The right ear microphone 14*b* outputs a noise signal, which is based on the detected noise, as the detection signal $e_R$ to the right ear high frequency control section 25*b*. The right ear high frequency control section 25*b* generates, based on the detection signal $e_R$, a control signal for controlling a level of the detection signal $e_R$ such that the level is lowered, the control signal having a higher frequency than a predetermined frequency. In other words, the right ear high frequency control section 25*b* generates a cancellation signal for canceling a noise arriving in the right ear case 12*b*, the noise having the higher frequency than the predetermined frequency. The right ear high frequency control section 25*b* outputs the generated control signal to the adder 21*b*. The adder 21*b* adds the control signal generated by the control section 15*a* to the control signal generated by the right ear high frequency control section 25*b*. A signal resulting from the addition at the adder 21*b* is inputted to the right ear speaker 13*b*. The right ear speaker 13*b* outputs sounds based on the control signals generated by the control section 15*a* and the right ear high frequency control section 25*b*. Here, as shown in FIG. 1, the noise arriving in the right ear case 12*b* is highly correlated, in the low frequency band, to the noise arriving in the left ear case 12*a*. Accordingly, near the right ear: a noise in the low frequency band, which has a high correlation, is canceled by the sound based on the control signal generated by the control section 15*a*; and the sound, which is based on the control signal generated by the right ear high frequency control section 25*b*, and a noise, which is in a frequency band of the control signal, are canceled by each other. Thus, the control section 15*a* generates a cancellation signal for common use between the vicinities of the left and right ears. The control section 15*a* corresponds to the first signal generation means of the present invention. Also, the left ear high frequency control section 25*a* and the right ear high frequency control section 25*b* each generate a cancellation signal for canceling a noise in a high frequency band, and each correspond to third signal generation means of the present invention. Here, there is only one control section 15*a* for the spaces formed for the left and right ears. Further, the left ear high frequency control section 25*a* and the right ear high frequency control section 25*b* are provided respectively corresponding to the two spaces formed for the left and right ears.

In the case where the sounds, which are based on the control signals, and the noises are not entirely canceled near the right ear, a control error is detected by the right ear microphone 14*b*, which control error is a residual component occurring as a result of synthesizing the sounds, which are based on the control signals, and the noises. The right ear microphone 14*b* outputs an error signal, which is based on the control error, as the detection signal $e_R$ to the right ear high frequency control section 25*b*. Thus, a feedback loop is formed near the right ear by the right ear microphone 14*b*, the right ear high frequency control section 25*b*, the adder 21*b* and the right ear speaker 13*b*. This feedback loop causes the noise control device to operate in such a manner that the control error near the right ear attenuates.

Figure 10:
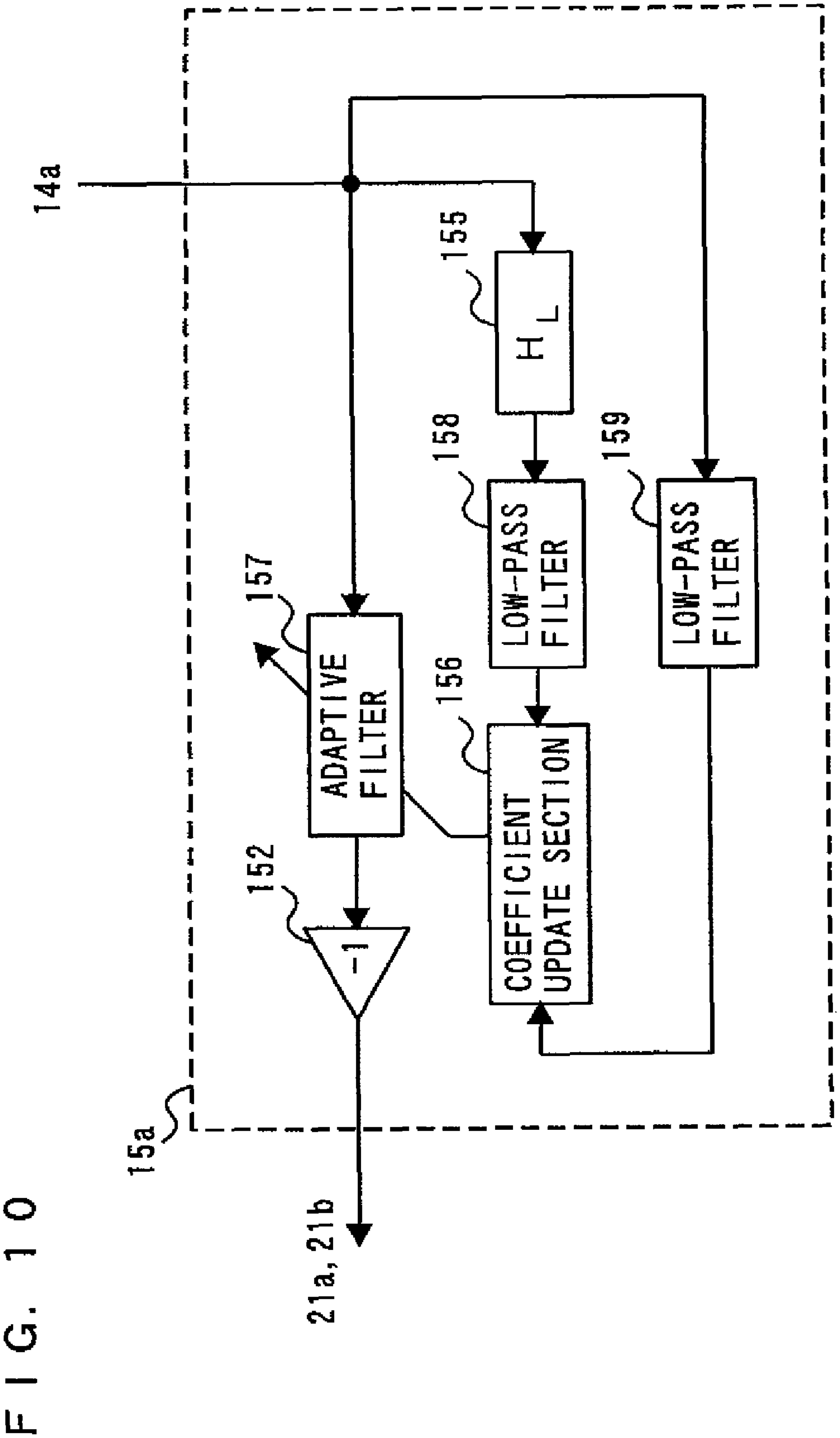

Next, the configuration of the control section 15*a* will be described with reference to FIG. 10. FIG. 10 shows the configuration of the control section 15*a*. Here, FIG. 10 shows, by way of example, the configuration in which the control section 15*a* is realized using an adaptive filter. The configuration of the control section 15*a* shown in FIG. 10 is a result of adding, to the configuration of the control section 15 shown in FIG. 6, low-pass filters 158 and 159. The low-pass filter 158 attenuates, from an output signal of the filtered X filter 155, a high frequency component higher than a predetermined frequency. The low-pass filter 159 attenuates, from an output signal of the left ear microphone 14*a*, a high frequency component higher than the predetermined frequency. For this reason, in the coefficient update section 156, a filter coefficient is rarely updated for the high frequency component higher than the predetermined frequency. This allows the filter coefficient calculated by the coefficient update section 156 to converge to such a filter coefficient that a gain is obtained only in a low frequency band no higher than the predetermined frequency. The filter coefficient calculated by the coefficient update section 156 is set as a filter coefficient for the adaptive filter 157. Accordingly, the control signal generated at the control section 15*a* is a signal which is generated based on a filter coefficient having an inverse characteristic to that of the electroacoustic transfer function $H_R$ and which has the frequency no higher than the predetermined frequency.

The left ear high frequency control section 25*a* and the right ear high frequency control section 25*b* are realized by replacing, in the configuration of the control section 15*a* shown in FIG. 10, the low-pass filters 158 and 159 with high-pass filters. The high-pass filters each attenuate a low-frequency component of an inputted signal, which is no higher than a predetermined frequency. For this reason, in the coefficient update section 156, a filter coefficient is rarely updated for the low-frequency component no higher than the predetermined frequency. Also, in the coefficient update section 156, a filter coefficient, which has an inverse characteristic to that of an electroacoustic transfer function having a phase lag in the high frequency band higher than the predetermined frequency, is updated. This allows the filter coefficient calculated by the coefficient update section 156 to converge to the filter coefficient which has the inverse characteristic to that of the electroacoustic transfer function having a phase lag and which allows a gain to be obtained only in the high frequency band higher than the predetermined frequency. The filter coefficient calculated by the coefficient update section 156 is set as a filter coefficient for the adaptive filter 157. Accordingly, the control signal generated at the left ear high frequency control section 25*a* is generated based on the filter coefficient having the inverse characteristic to that of the electroacoustic transfer function $H_L$ having a phase lag, and has the higher frequency than the predetermined frequency. Also, the control signal generated at the right ear high frequency control section 25*b* is generated based on the filter coefficient having the inverse characteristic to that of the electroacoustic transfer function $H_R$ having a phase lag, and has the higher frequency than the predetermined frequency.

As described above, separately for the high frequency band higher than the predetermined frequency in which the phase of the electroacoustic transfer function is lagged, the noise control device according to the present embodiment performs a control using the left ear high frequency control section 25*a* and the right ear high frequency control section 25*b* for each of which the filter coefficient based on the electroacoustic transfer function having a phase lag is set. In other words, the control section 15*a*, and the left and right ear high frequency control sections 25*a* and 25*b*, divide the frequency band, and the control signal is generated for each divided frequency band. This enables an optimal control to be performed in accordance with the phase lag of the electroacoustic transfer function. This consequently allows a frequency band, in which the noise reduction effect is obtained, to be further widened as compared to the first embodiment. Moreover, according to the noise control device of the present embodiment, the control section 15*a* is only required to generate the control signal whose frequency is no higher than the predetermined frequency. This reduces a processing load of the control section 15*a* as compared to a processing load of the control section 15 according to the first embodiment.

Figure 11:
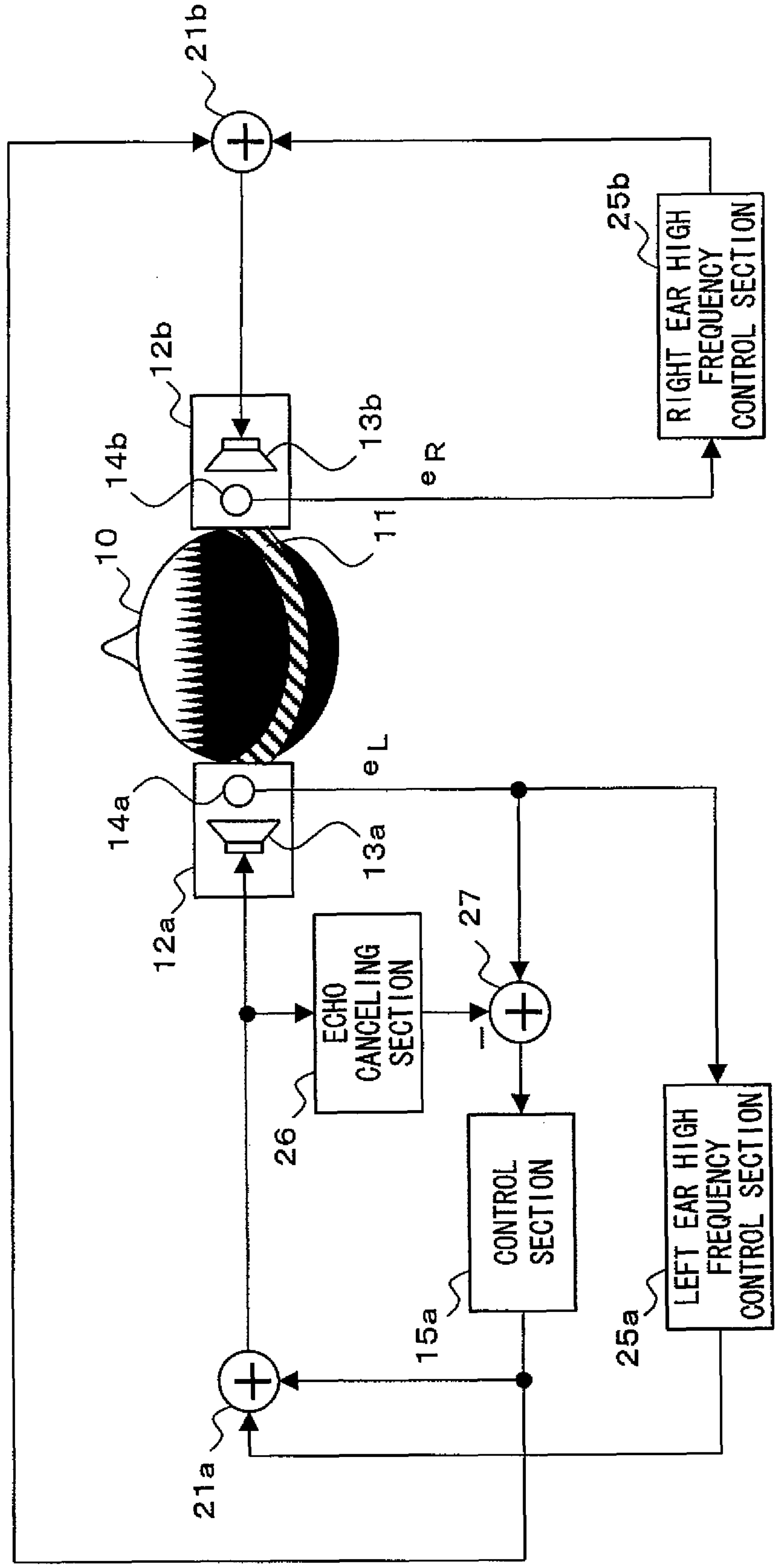
FIG. 11 shows a configuration which is a result of further adding, to the configuration of the noise control device shown in FIG. 9, an echo canceling section 26 and a subtractor 27.

Note that, the configuration of the noise control device shown in FIG. 9 may additionally have an echo canceling section 26 and a subtractor 27 as shown in FIG. 11. FIG. 11 shows a configuration which is a result of adding, to the configuration of the noise control device shown in FIG. 9, the echo canceling section 26 and the subtractor 27. The echo canceling section 26 cancels echo which contributes to howling, and has the same function as that of the echo cancellation filter 153 shown in FIG. 5. For the echo canceling section 26, a filter coefficient indicating the transfer function $E_L$ is set. The transfer function $E_L$ is set so as to simulate the electroacoustic transfer function $H_L$ at the left ear. The echo canceling section 26 processes, based on the filter coefficient indicating the transfer function $E_L$, an output signal from the adder 21*a*, and outputs the processed signal to the subtractor 27. The subtractor 27 subtracts, from the detection signal $e_L$, outputted from the left ear microphone 14*a*, the output signal of the echo canceling section 26. By additionally having the echo canceling section 26 as described above, processing can be stabilized for the feedback loop including the control section 15*a* and the feedback loop including the left ear high frequency control section 25*a*. Consequently, an occurrence of an unusual sound due to oscillation, such as howling, can be suppressed.

Third Embodiment

Hereinafter, the noise control device according to a third embodiment of the present invention will be described with reference to the drawings. The noise control device according to the present embodiment is, as compared to the above second embodiment, further capable of producing an optimal noise reduction effect in accordance with an arrival direction of noise.

Figure 12:
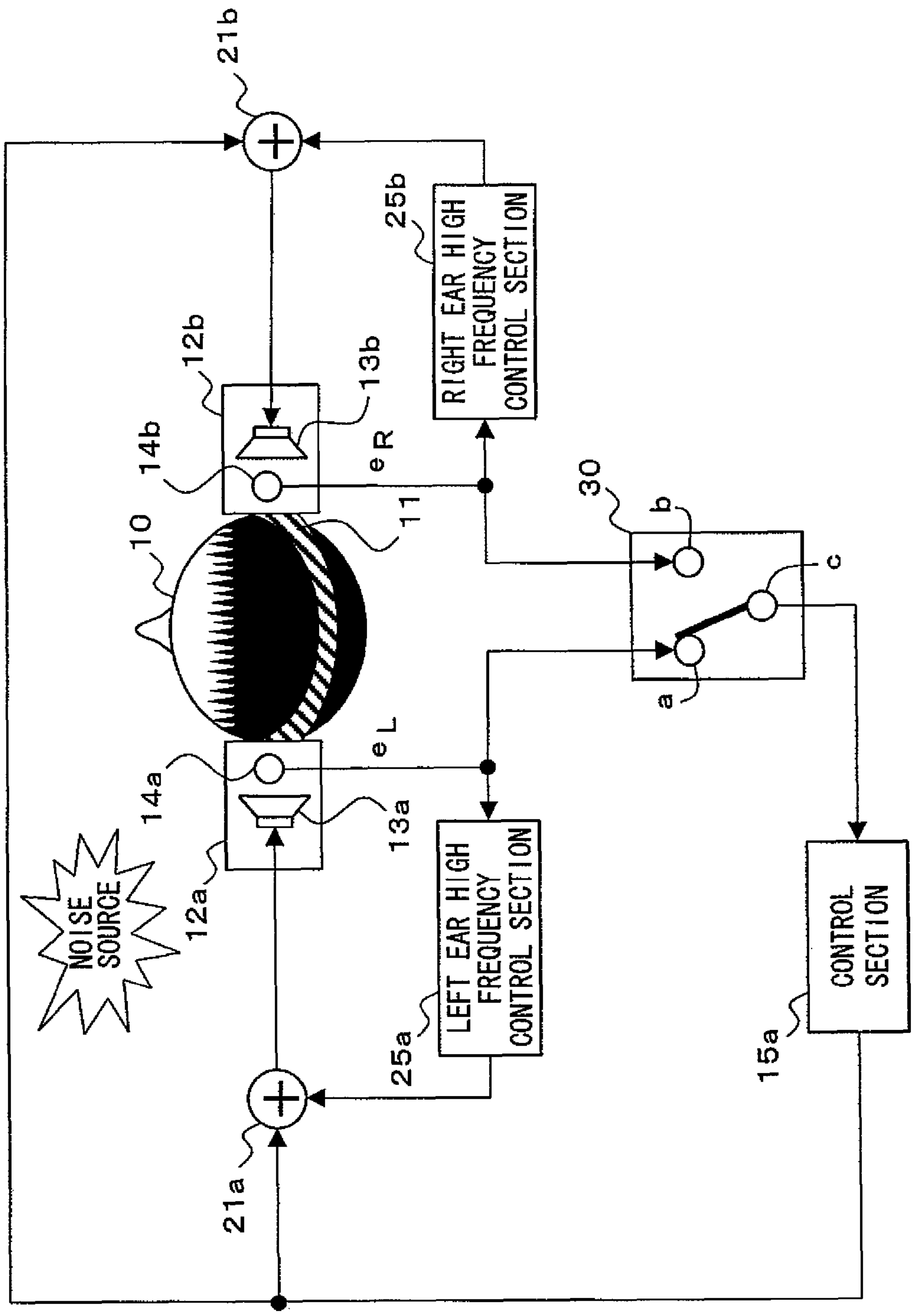
FIG. 12 shows a configuration of a noise control device according to a third embodiment.

A configuration of the noise control device according to the third embodiment will be described with reference to FIG. 12. FIG. 12 shows a configuration of the noise control device according to the third embodiment. As shown in FIG. 12, the noise control device comprises the headband 11, the left ear case 12*a*, the right ear case 12*b*, the left ear speaker 13*a*, the right ear speaker 13*b*, the left ear microphone 14*a*, the right ear microphone 14*b*, the control section 15*a*, the adders 21*a* and 21*b*, the left ear high frequency control section 25*a*, the right ear high frequency control section 25*b*, and a switching section 30. The configuration shown in FIG. 12 is different from the second embodiment shown in FIG. 9 in that the configuration shown in FIG. 12 newly comprises the switching section 30. It is assumed for FIG. 12 that components, which are denoted by the same reference numerals as those used for components shown in FIG. 9, have the same functions as those of the components shown in FIG. 9, and descriptions thereof will be omitted. Note that, FIG. 12 and later-described FIGS. 13A, 15 and 17 each are a diagram which shows a view seen from above a head of the user 10 and in which the user 10 faces upward. Hereinafter, a description will be given with a focus on the aforementioned difference.

The switching section 30 switches, between an output of the left ear microphone 14*a* and an output of the right ear microphone 14*b*, an output of a microphone to be connected to an input of the control section 15*a*. The switching section 30 is provided with terminals a to c. The input of the control section 15*a* is connected to the terminal c. The output of the left ear microphone 14*a* is connected to the terminal a. The output of the right ear microphone 14*b* is connected to the terminal b. The switching section 30 switches a connection state by connecting the terminals a and c, or by connecting the terminals b and c. Which connection state is to be used is determined based on an operation by the user 10. FIG. 12 shows the connection state of the switching section 30 in which the terminals a and c are connected.

Figure 13A:
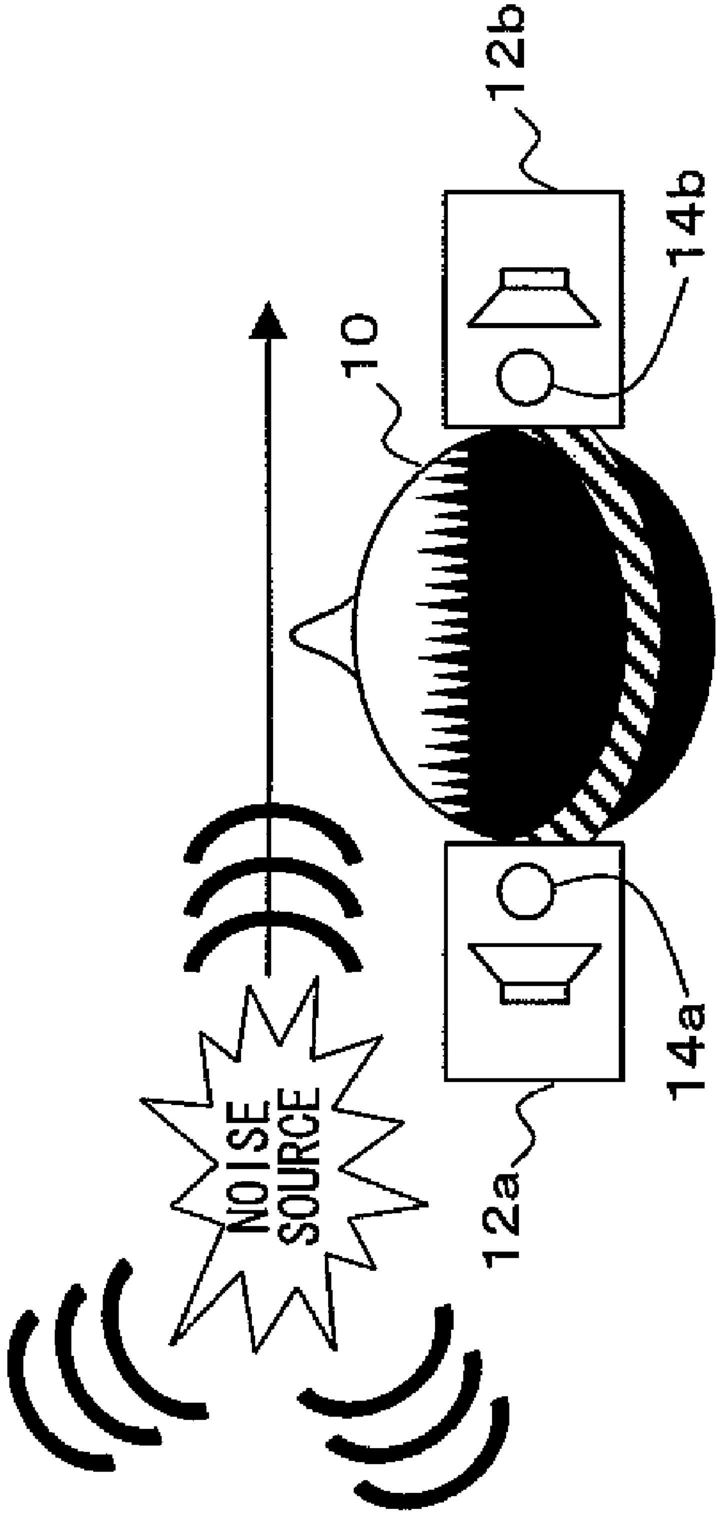
FIG. 13A shows a state where there is a noise source at a left ear side of a user 10.
Figure 13B:
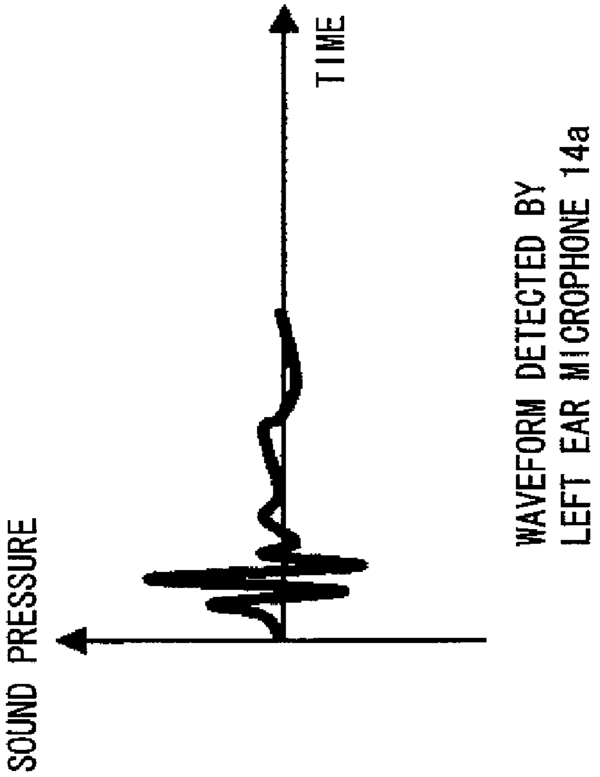
FIG. 13B shows a waveform, along a temporal axis, of a noise which is detected by a left ear microphone 14a in an environment illustrated in FIG. 13A.
Figure 13C:
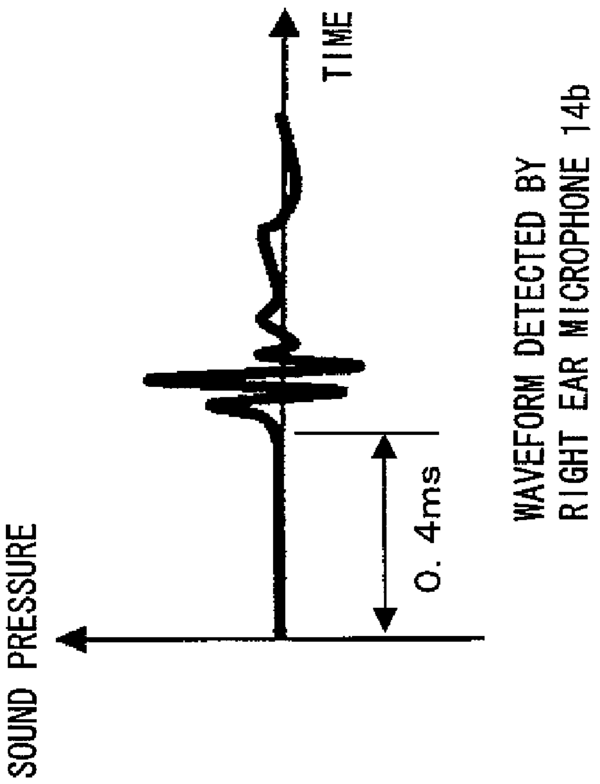
FIG. 13C shows a waveform, along a temporal axis, of a noise which is detected by a right ear microphone 14b in the environment illustrated in FIG. 13A.

Next, a relationship between the connection state of the switching section 30 and a noise reduction operation will be described with reference to FIGS. 12 and 13A-C. It is assumed in the following description that there is an environment where a noise source is present at the left ear side of the user 10 as shown in FIG. 12. FIGS. 13A-C are diagrams for describing the relationship between the connection state of the switching section 30 and the noise reduction operation. FIG. 13A shows a state where there is a noise source at the left ear side of the user 10. FIG. 13B shows a waveform, along a temporal axis, of a noise detected by the left ear microphone 14*a* in the environment illustrated in FIG. 13A. FIG. 13C shows a waveform, along a temporal axis, of a noise detected by the right ear microphone 14*b* in the environment illustrated in FIG. 13A.

In the environment where the noise source is present at the left ear side of the user 10, a noise generated from the noise source is transmitted from the left side to the right side of the user 10. Generally speaking, a distance between the left and right ears of the user 10 is 15 cm. Accordingly, when it is assumed that a sound velocity is 340 m/sec, there is a time lag of approximately 0.4 ms between a timing at which a noise is detected by the left ear microphone 14*a* and a timing at which the noise is detected by the right ear microphone 14*b*. In other words, as shown in FIGS. 13B and 13C, the timing of detection at the right ear microphone 14*b* is delayed, by approximately 0.4 ms, from the timing of detection at the left ear microphone 14*a*.

When the connection state of the switching section 30 is such that the terminals a and c are connected as shown in FIG. 12, the control section 15*a* generates a control signal by using the detection signal $e_L$ of the left ear microphone 14*a*. Here, it is ideal that the right ear speaker 13*b* radiates, at a same timing as that when a noise arrives near the left ear, a sound based on the control signal generated by using the detection signal $e_L$ of the left ear microphone 14*a*. Accordingly, the noise to be controlled arrives near the right ear when 0.4 ms have passed after the timing of radiation, from the right ear speaker 13*b*, of the sound based on the control signal.

On the other hand, when the connection state of the switching section 30 is such that the terminals b and c are connected, the control section 15*a* generates a control signal by using the detection signal $e_R$ of the right ear microphone 14*b*. Here, it is ideal that the right ear speaker 13*b* radiates, at a same timing as that when the noise arrives near the right ear, a sound based on the control signal generated by using the detection signal $e_R$ of the right ear microphone 14*b*. In other words, the timing at which the noise arrives near the right ear is the same as the timing at which the right ear speaker 13*b* radiates, near the right ear, the sound based on the control signal.

In reality, however, there is a delay time from when the microphone detects a noise to when the speaker outputs the sound based on the control signal, due to a processing delay such as a processing delay at the control section 15*a* or a group delay of an electroacoustic transfer function.

Accordingly, in the case where the connection state of the switching section 30 is such that the terminals a and c are connected as shown in FIG. 12, if the delay time due to the aforementioned processing delay is approximately 0.4 ms, the delay time due to the processing delay is compensated for by the delay time occurring in the case of the connection state shown in FIG. 12. To be specific, in reality, in the case of the connection state shown in FIG. 12, the timing at which the right ear speaker 13*b* radiates the sound based on the control signal is the same as the timing at which the noise arrives near the right ear.

Note that, near the left ear, the delay time caused by the aforementioned processing delay is not compensated for. In other words, in the case of the connection state shown in FIG. 12, near the left ear, the timing at which the left ear speaker 13*a* radiates the sound based on the control signal is delayed, by the above processing delay (0.4 ms), from the timing at which the noise arrives near the left ear. Accordingly, a level of noise reduction is lower near the left ear than near the right ear.

On the other hand, when the connection state of the switching section 30 is such that the terminals b and c are connected, the timing at which the right ear speaker 13*b* radiates, near the right ear, the sound based on the control signal is delayed, by the above processing delay (0.4 ms), from the timing at which the noise arrives near the right ear.

Note that, near the left ear, the timing at which the left ear speaker 13*a* radiates the sound based on the control signal is delayed from the timing at which the noise arrives near the left ear, by the sum (0.8 ms) of the above processing delay (0.4 ms) and the delay time (0.4 ms) for the noise to arrive near the right ear from the left ear. In other words, a level of noise reduction is lower near the left ear than near the right ear.

Provided below is a comparison, between the case where the connection state of the switching section 30 is such that the terminals a and c are connected and the case where the connection state of the switching section 30 is such that the terminals b and c are connected, about the delay time between the timing at which the speaker radiates the sound based on the control signal and the timing at which the noise arrives. As described above, in the case where the connection state of the switching section 30 is such that the terminals a and c are connected, the delay time near the right ear is 0, and the delay time near the left ear is the aforementioned processing delay (0.4 ms). On the other hand, as described above, in the case where the connection state of the switching section 30 is such that the terminals b and c are connected, the delay time near the right ear is the aforementioned processing delay (0.4 ms), and the delay time near the left ear is the sum (0.8 ms) of the above processing delay (0.4 ms) and the delay time (0.4 ms) for the noise to arrive near the right ear from the left ear. Accordingly, the level of noise reduction is higher in the case where the connection state of the switching section 30 is such that the terminals a and c are connected, i.e., in the case of performing a control by using the left ear microphone 14*a* which is a nearest microphone to the noise source.

Figure 14A:
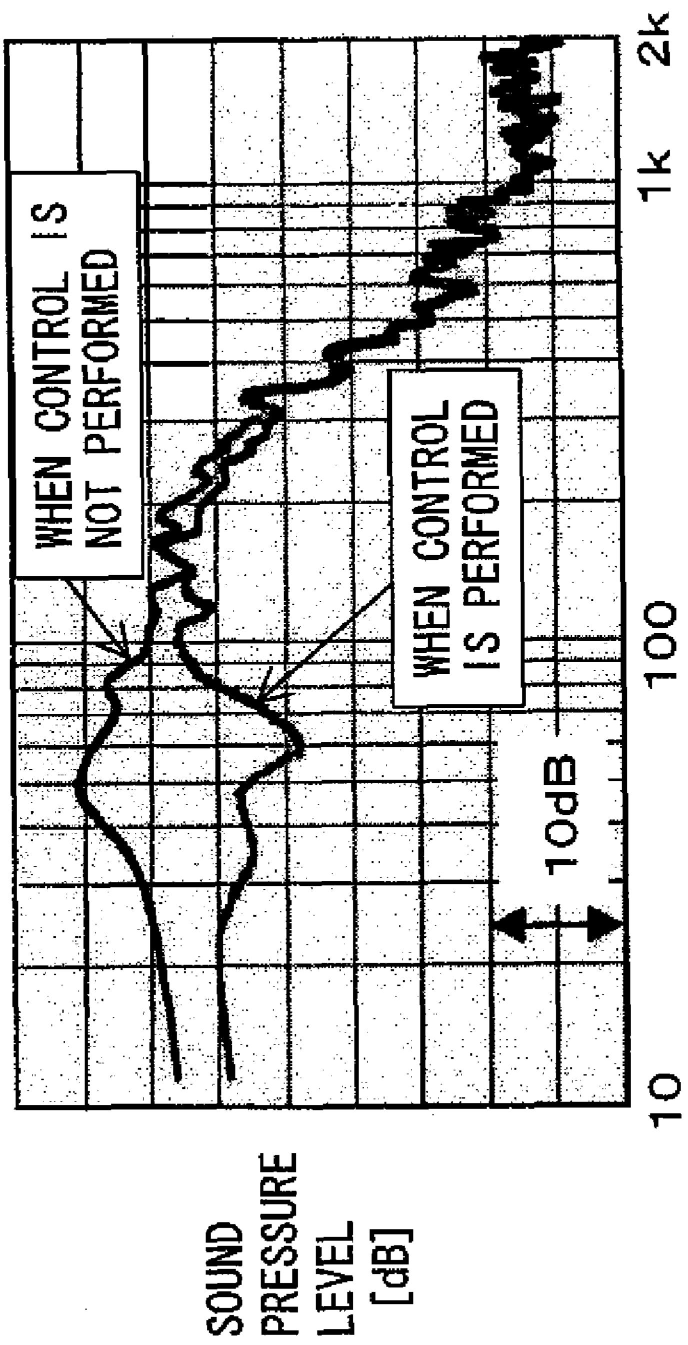
Figure 14B:
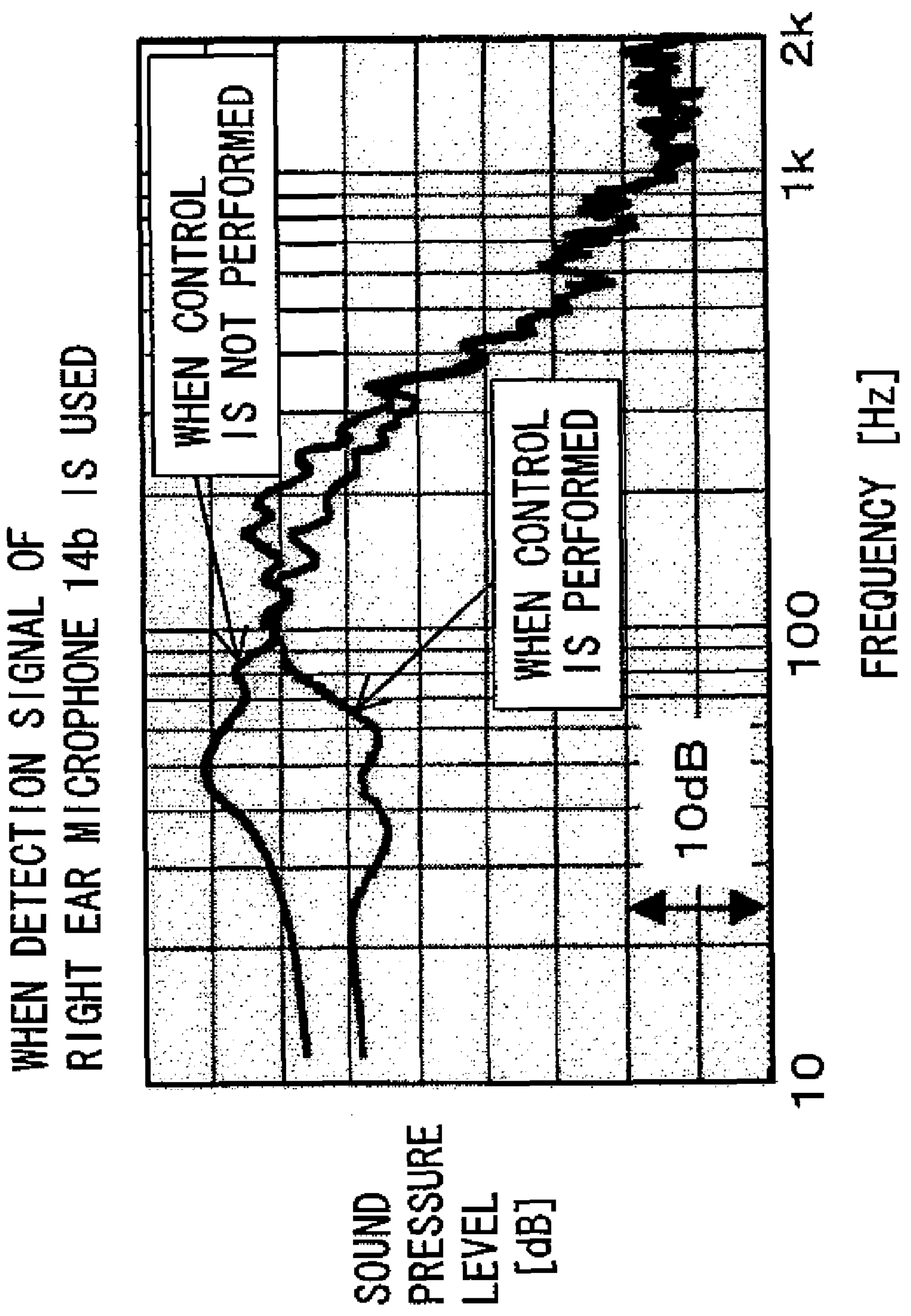
FIG. 14B shows a frequency characteristic of the detection signal $e_L$ of the left ear microphone 14a in the case where a control is performed using the detection signal $e_R$ of the right ear microphone 14b.

FIG. 14A shows a frequency characteristic of the detection signal $e_R$ of the right ear microphone 14*b* in the case where a control is performed using the detection signal $e_L$ of the left ear microphone 14*a*, in the environment where the noise source is present at the left ear side of the user 10. FIG. 14B shows a frequency characteristic of the detection signal $e_L$ of the left ear microphone 14*a* in the case where a control is performed using the detection signal $e_R$ of the right ear microphone 14*b*, in the environment where the noise source is present at the left ear side of the user 10. It is understood from these diagrams that in the case where the detection signal shown in FIG. 14A is used when the control is performed, a frequency band, in which a sound pressure level decreases as compared to when the control is not performed, is wider, and an amount, by which the sound pressure level decreases as compared to when the control is not performed, is greater. In other words, the detection signal shown in FIG. 14A is superior with respect to the width of the frequency band in which the noise is reduced and to the amount of the noise reduction.

When it is assumed that there is an environment where there is a noise source at the right ear side of the user 10, the switching section 30 may switch, in accordance with an operation by the user 10, the output of the microphone to be connected to the input of the control section 15*a*, to the output of the right ear microphone 14*b* which is the nearest microphone to the noise source. Further, even if the noise control device has three or more microphones, the switching section 30 may switch, in accordance with an operation by the user 10, the output of the microphone to be connected to the input of the control section 15*a*, to the output of a nearest microphone to the noise source.

As described above, in the noise control device according to the present embodiment, the switching section 30 may switch, in accordance with an operation by the user 10, the output of the microphone to be connected to the input of the control section 15*a*, to the output of the nearest microphone to the noise source. This produces an optimal noise reduction effect in accordance with an arrival direction of the noise.

Figure 15:
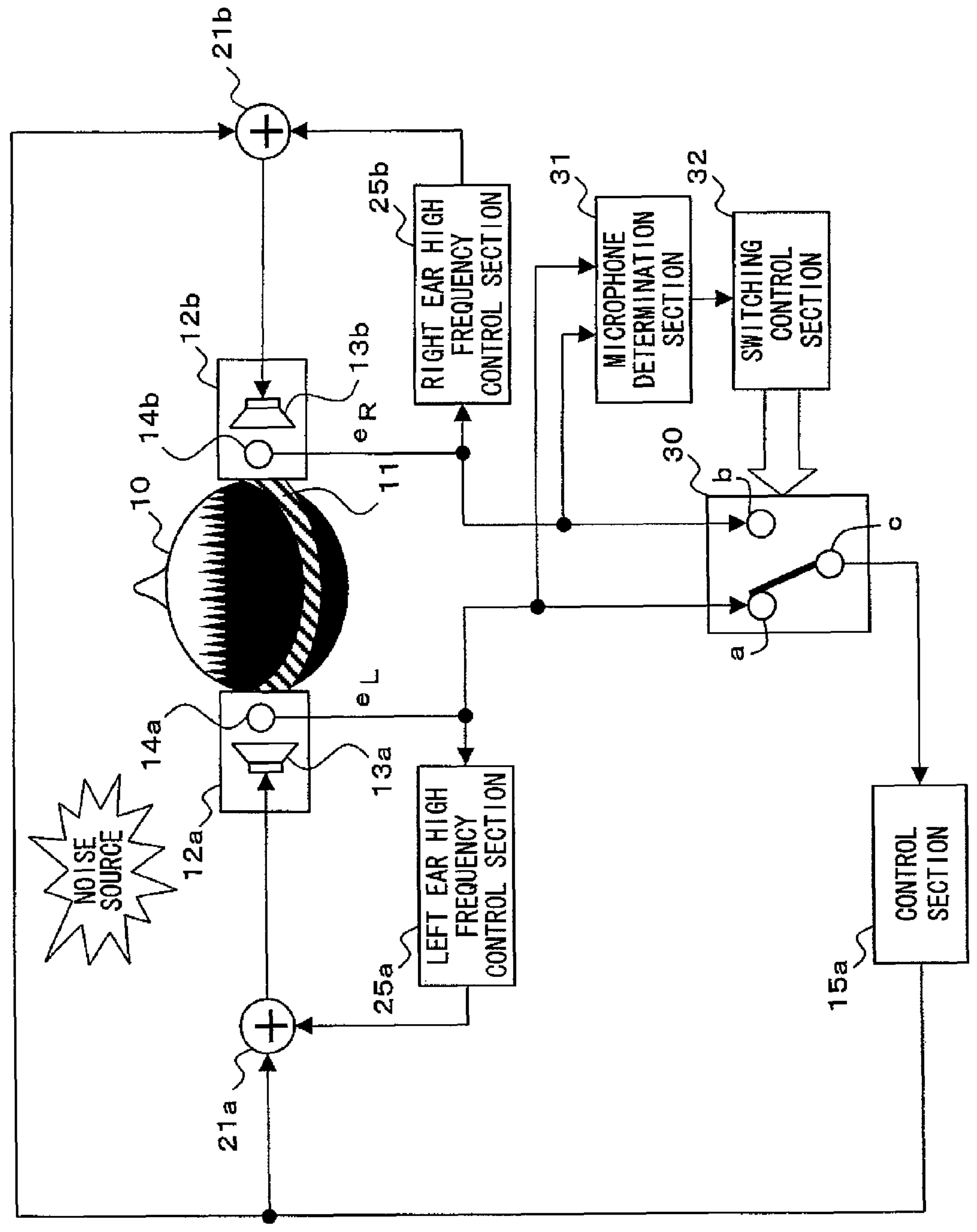
FIG. 15 shows a configuration which is a result of newly adding a microphone determination section 31 and a switching control section 32 to the configuration shown in FIG. 12.

In the above description, the switching section 30 switches the connection in accordance with an operation by the user 10. However, in the case where the user 10 is unable to specify a position of the noise source, a microphone determination section 31 and a switching control section 32 may be newly added. FIG. 15 shows a configuration which is a result of newly adding the microphone determination section 31 and the switching control section 32 to the configuration shown in FIG. 12.

In FIG. 15, the microphone determination section 31 refers to the detection signal $e_L$ of the left ear microphone 14*a* and the detection signal $e_R$ of the right ear microphone 14*b*, thereby determining whether the nearest microphone to the noise source is the left ear microphone 14*a* or the right ear microphone 14*b*. Hereinafter, a manner of the determination performed by the microphone determination section 31 will be described. It is assumed here that an initial state of the noise control device shown in FIG. 15 is such that the terminals a and c or the terminals b and c are connected in the switching section 30. The microphone determination section 31 analyzes a frequency of the detection signal $e_L$ of the left ear microphone 14*a* and a frequency of the detection signal $e_R$ of the right ear microphone 14*b*. The microphone determination section 31 compares, at a frequency f in a frequency band for which the control section 15*a* performs a control, a sound pressure level of the detection signal $e_L$ of the left ear microphone 14*a* and a sound pressure level of the detection signal $e_R$ of the right ear microphone 14*b*.

Here, as described above, regardless of whether the terminals a and c are connected or the terminals b and c are connected in the switching section 30, the level of noise reduction is lower for an ear which is nearer to the noise source than the other ear. In other words, regardless of whether the terminals a and c are connected or the terminals b and c are connected in the switching section 30, the sound pressure level of the detection signal of the nearer microphone to the noise source is higher than the sound pressure level of the detection signal of the other microphone. Therefore, the microphone determination section 31 determines that a microphone whose sound pressure level is higher is the nearest microphone to the noise source.

Figure 16:
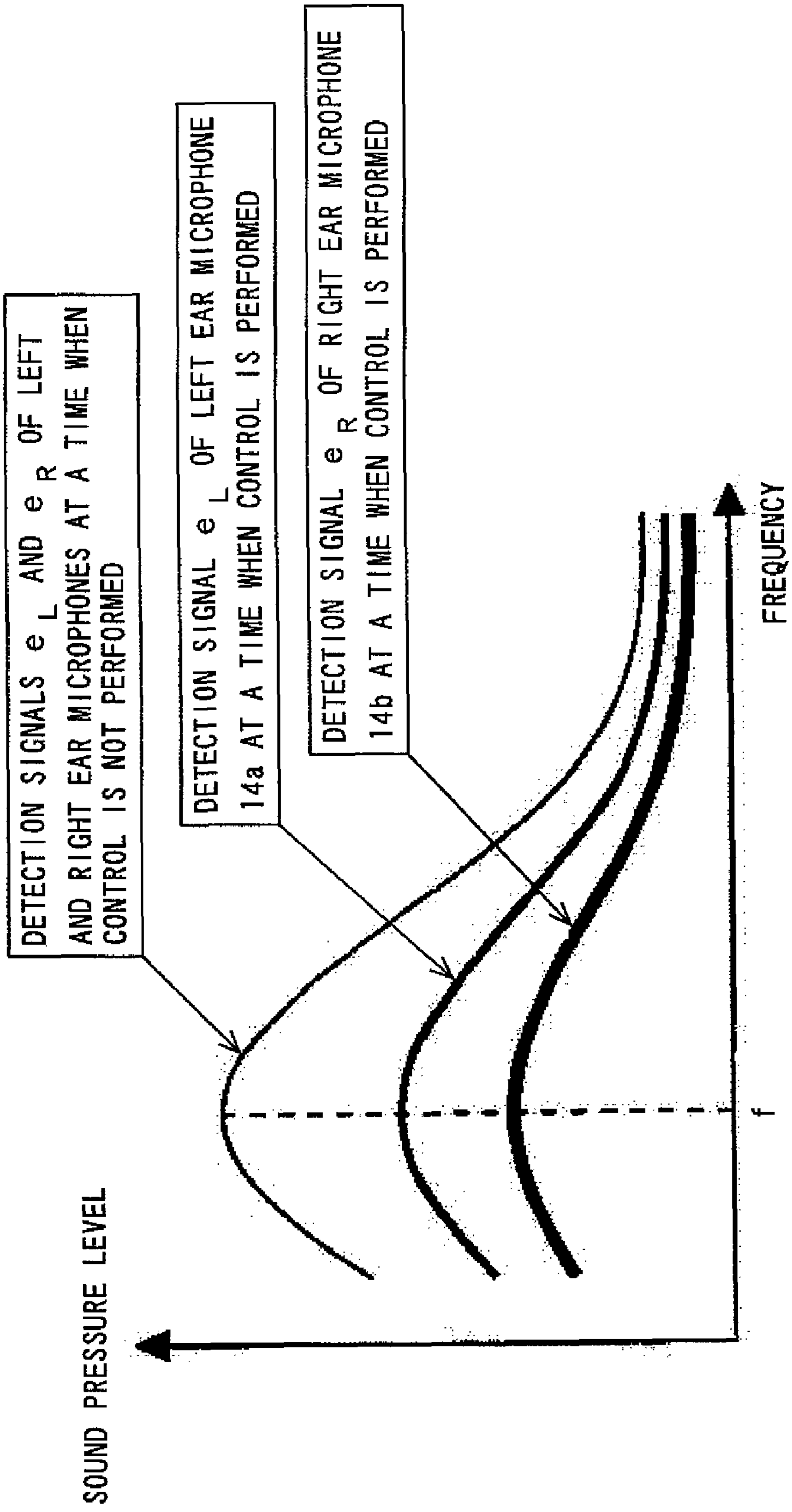
FIG. 16 shows a result of analyzing, when control is performed, frequencies of the detection signal $e_L$ of the left ear microphone 14a and the detection signal $e_R$ of the right ear microphone 14b, and a result of analyzing, when the control is not performed, the frequencies of the detection signal $e_L$ of the left ear microphone 14a and the detection signal $e_R$ of the right ear microphone 14b.

FIG. 16 shows: a result of analyzing, when the control is not performed, the frequencies of the detection signal $e_L$ of the left ear microphone 14*a* and the detection signal $e_R$ of the right ear microphone 14*b*; a result of analyzing, when the control is performed, the frequency of the detection signal $e_L$ of the left ear microphone 14*a*; and a result of analyzing, when the control is performed, the frequency of the detection signal $e_R$ of the right ear microphone 14*b*. In an example shown in FIG. 16, when the control is not performed, the sound pressure level of the detection signal $e_L$ of the left ear microphone 14*a* is the same as the sound pressure level of the detection signal $e_R$ of the right ear microphone 14*b*. On the other hand, when the control is performed, the sound pressure level of the detection signal $e_L$ of the left ear microphone 14*a* is higher than that of the detection signal $e_R$ of the right ear microphone 14*b*. Therefore, in the example shown in FIG. 16, the microphone determination section 31 determines that the left ear microphone 14*a* is the nearest microphone to the noise source.

Based on a determination result provided by the microphone determination section 31, the switching control section 32 controls the switching section 30 such that the output of the microphone to be connected to the input of the control section 15*a* is switched to the output of the nearest microphone to the noise source.

As described above, by having the configuration shown in FIG. 15, the output of the microphone to be connected to the input of the control section 15*a* can be automatically switched to the output of the nearest microphone to the noise source, even if the user 10 is unable to specify the position of the noise source.

Note that, in the configuration shown in FIG. 15, the switching operation by the microphone determination section 31 and the switching control section 32 may be performed only when the noise control device performs an initial operation, or may be performed regularly.

Further, in the configuration shown in FIG. 15, the microphone determination section 31 compares the sound pressure levels of the detection signals of the left ear microphone 14*a* and the right ear microphone 14*b*. However, the present invention is not limited thereto. The microphone determination section 31 may perform a determination by using a cross-correlation function related to the detection signals. In such a case, the microphone determination section 31 first calculates the cross-correlation function for the detection signals of the left ear microphone 14*a* and the right ear microphone 14*b*. The microphone determination section 31 uses the cross-correlation function, thereby calculating a time lag between the detection signals, based on a characteristic of the cross-correlation function in which a maximum value of the time lag between the detection signals is taken. The microphone determination section 31 evaluates a noise arrival direction from the calculated time lag, and determines the nearest microphone to the noise source. Still further, the microphone determination section 31 may determine the nearest microphone to the noise source, based on, e.g., seat position information in a vehicle such as an aircraft. The seat position information may indicate, e.g., a right or left side seat, or aisle or window seat. In the case of, e.g., a window seat, a noise source exists at a window side, and therefore the microphone determination section 31 determines that the nearest microphone to the window is the nearest microphone to the noise source.

Although the configurations shown in FIGS. 12 and 15 each comprise the left ear high frequency control section 25*a* and the right ear high frequency control section 25*b*, these components may be omitted therefrom.

Figure 17:
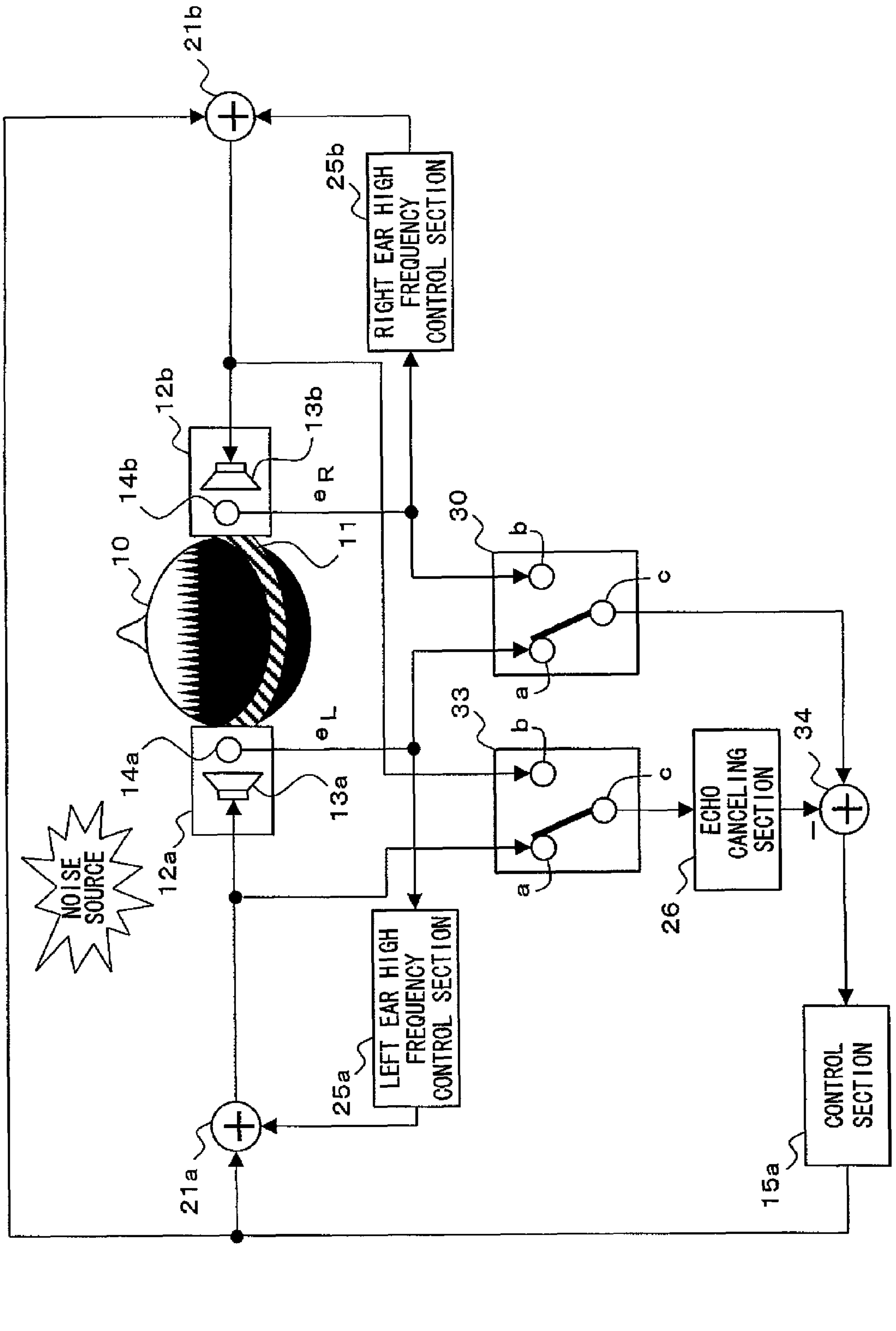
FIG. 17 shows a configuration which is a result of newly having, in the configurations shown in FIGS. 12 and 15, an echo canceling section 26 described in the second embodiment.

Still further, the configurations shown in FIGS. 12 and 15 may each newly comprise, as shown in FIG. 17, the echo canceling section 26 described in the second embodiment. FIG. 17 shows a configuration which is a result of newly having, to the configurations shown in FIGS. 12 and 15, the echo canceling section 26 described in the second embodiment. In this case, as shown in FIG. 17, the configuration shown in FIG. 12 newly comprises the echo canceling section 26, a switching section 33 and a subtractor 34. The switching section 33 switches a connection of the echo canceling section 26 such that the echo canceling section 26 is connected to an output of the adder 21*a* or an output of the adder 21*b*. The switching section 33 is provided with terminals a to c. An input of the echo canceling section 26 is connected to the terminal c. The output of the adder 21*a* is connected to the terminal a. The output of the adder 21*b* is connected to the terminal b. The switching section 33 switches a connection state thereof by either connecting the terminals a and c or connecting the terminals b and c. Note that, the switching section 33 switches the connection state thereof in conjunction with the switching section 30. To be specific, when the connection state of the switching section 30 is such that the terminals a and c are connected, the connection state of the switching section 33 is also such that the terminals a and c are connected. Further, when the connection state of the switching section 30 is such that the terminals b and c are connected, the connection state of the switching section 33 are also such that the terminals b and c are connected. The subtractor 34 subtracts an output signal of the echo canceling section 26 from an output signal of the switching section 30.

Fourth Embodiment

Hereinafter, a noise control device according to a fourth embodiment of the present invention will be described with reference to the drawings. Described in the present embodiment are other forms of noise control devices which are further developed using the noise control devices according to the above first to third embodiments.

Figure 18:
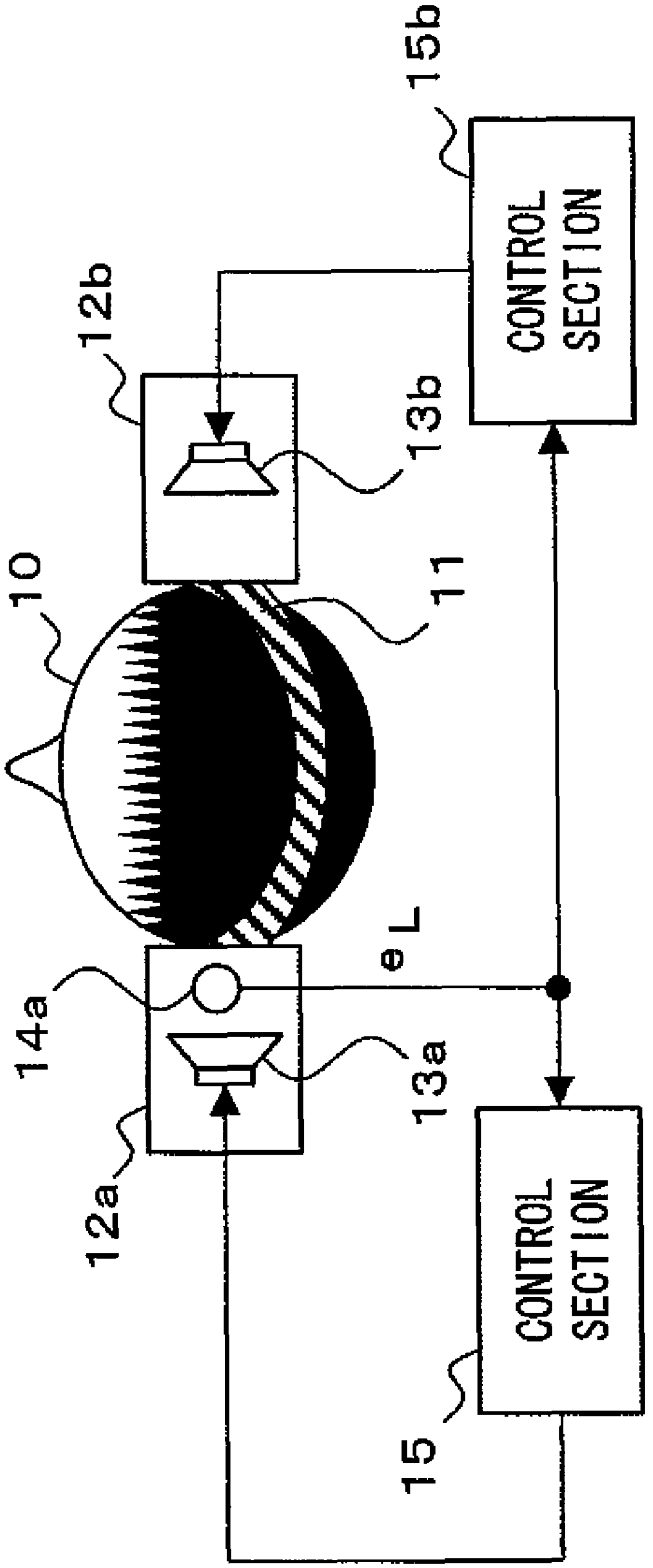
FIG. 18 shows a configuration of a first use form in which the noise control device according to the first embodiment is used.

A first use form will be described with reference to FIG. 18. FIG. 18 shows a configuration of the first use form in which the noise control device according to the first embodiment is used. The configuration shown in FIG. 18 is a result of adding a control section 15*b* to the configuration shown in FIG. 2. It is assumed for FIG. 18 that components, which are denoted by the same reference numerals as those used for components of the noise control device of the first embodiment in FIG. 2, have the same functions as those of the components of the noise control device in FIG. 2, and descriptions thereof will be omitted. FIG. 18 shows a view seen from above a head of the user 10. In FIG. 18, the user 10 faces upward.

The control section 15*b* has the same configuration as that of the control section 15 described with reference to FIG. 3, except that a filter coefficient, which has an inverse characteristic to that of the electroacoustic transfer function $H_R$ of the right ear speaker 13*b*, is set for a feedback control filter of the control section 15*b*. The control section 15*b* generates, based on the detection signal $e_L$, a control signal for controlling a level of the detection signal $e_L$ detected by the left ear microphone 14*a* such that the level is lowered. The control signal generated by the control section 15*b* is outputted to the right ear speaker 13*b*.

According to the configuration shown in FIG. 18, even if there is a significant characteristic difference between the left ear speaker 13*a* and the right ear speaker 13*b*, noise can be reduced for both the left and right ears. Further, since only one microphone is used for detecting a noise, there is an advantage of reducing a cost for a microphone, as compared to the above-described conventional art.

Figure 19:
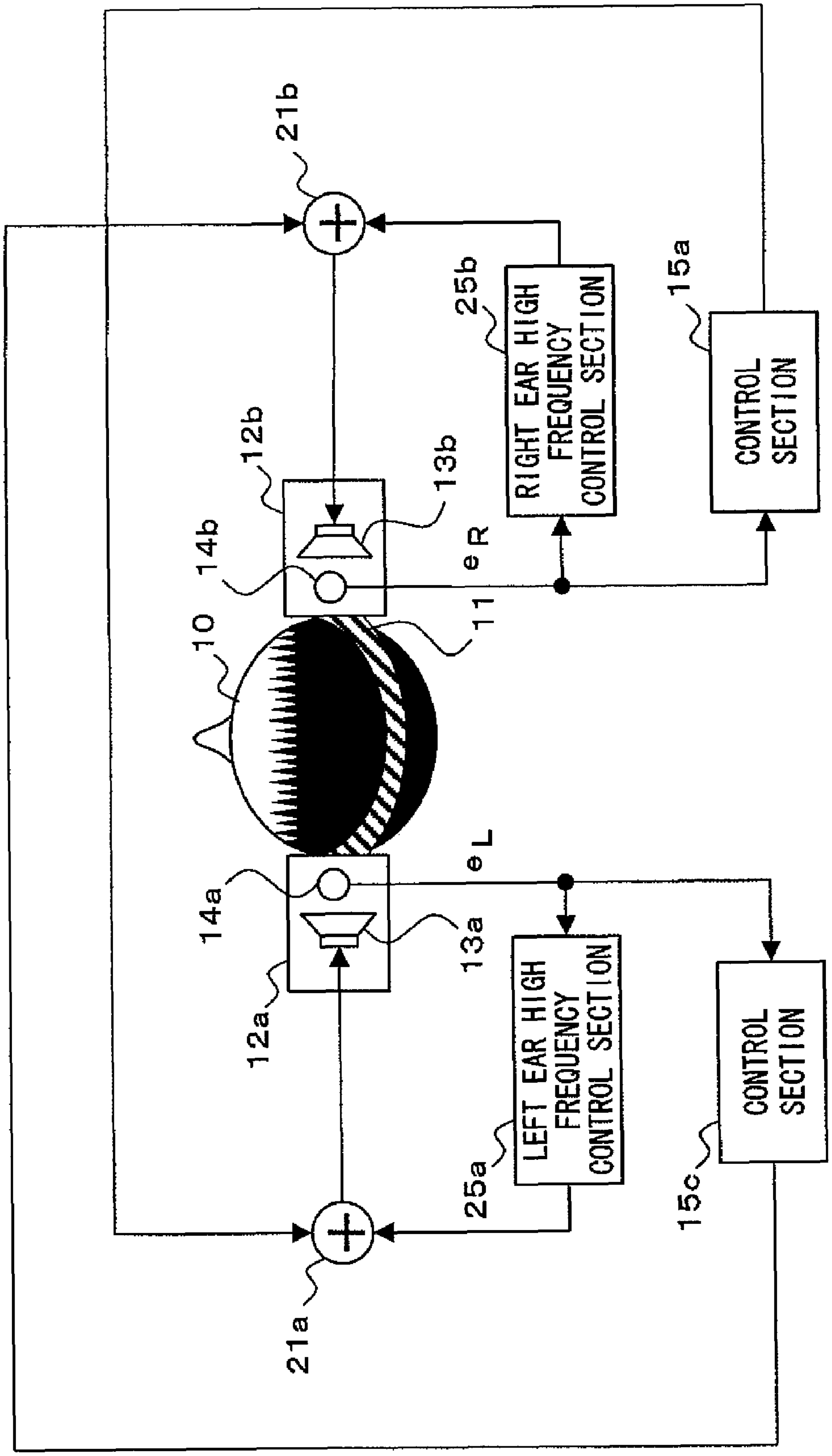
FIG. 19 shows a configuration of a second use form which is further developed from the noise control device according to the second embodiment.
Figure 20:
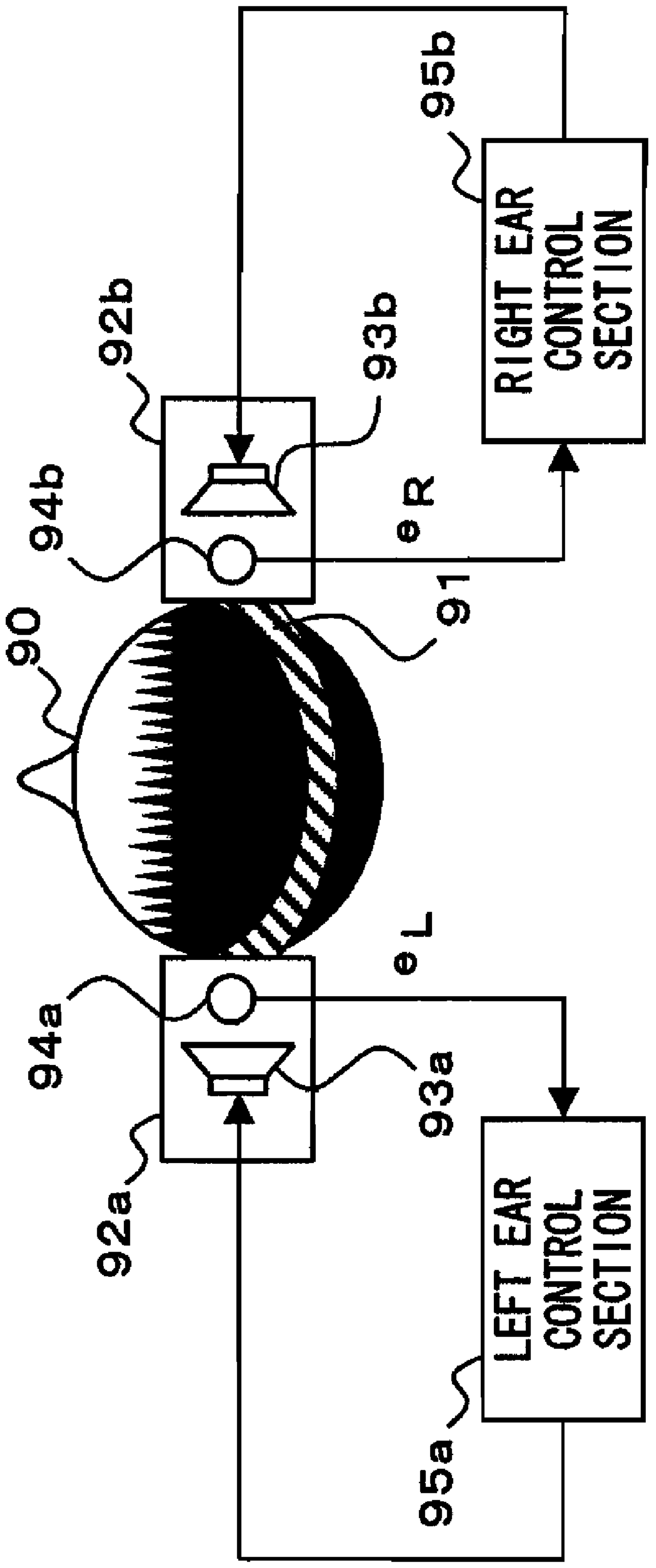
FIG. 20 PRIOR ART
FIG. 20 shows a configuration of a conventional noise-canceling headphone.
Figure 21:
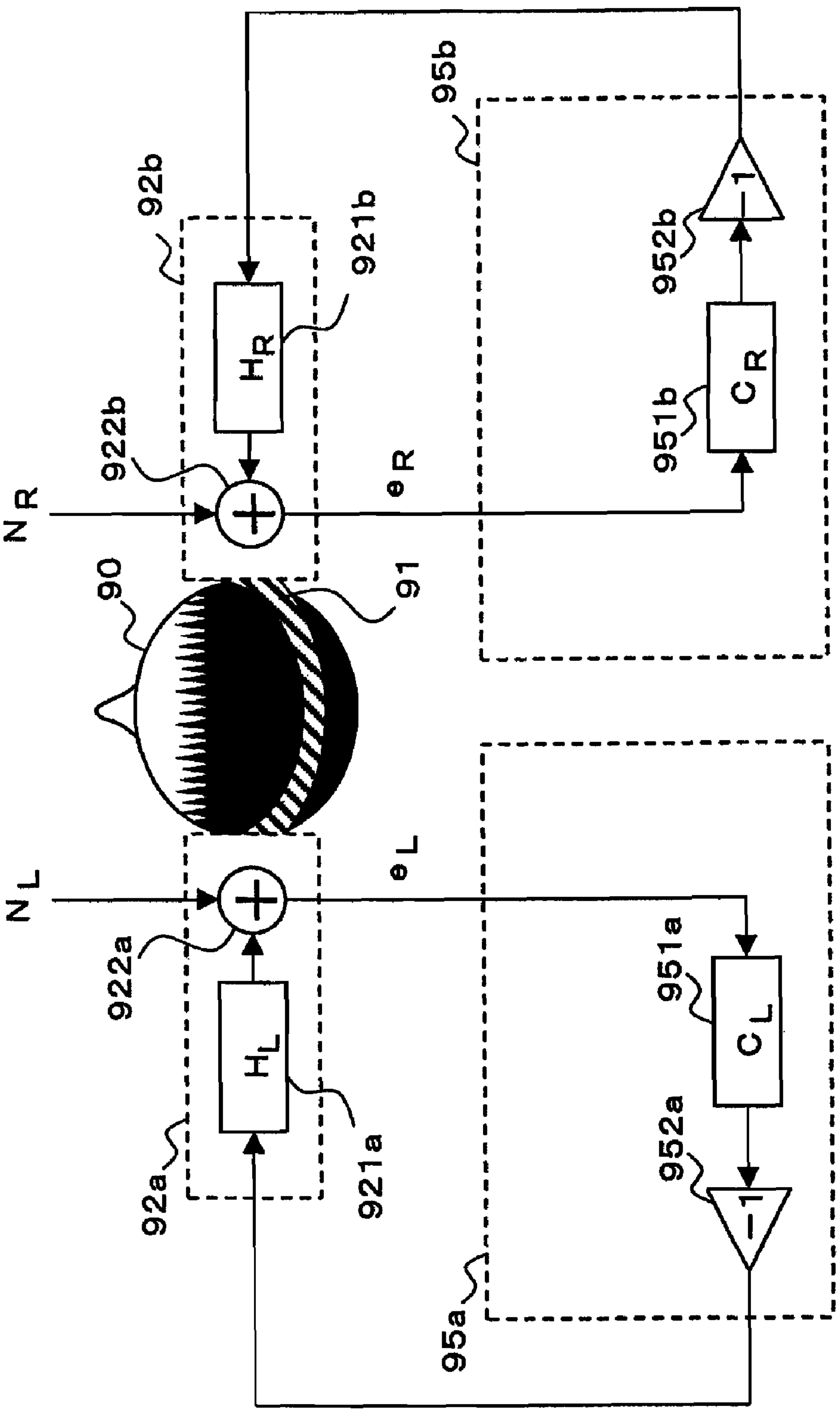
FIG. 21 PRIOR ART
FIG. 21 shows, by blocks of signal processing, the configuration of the noise-canceling headphone of FIG. 20.
Figure 22:
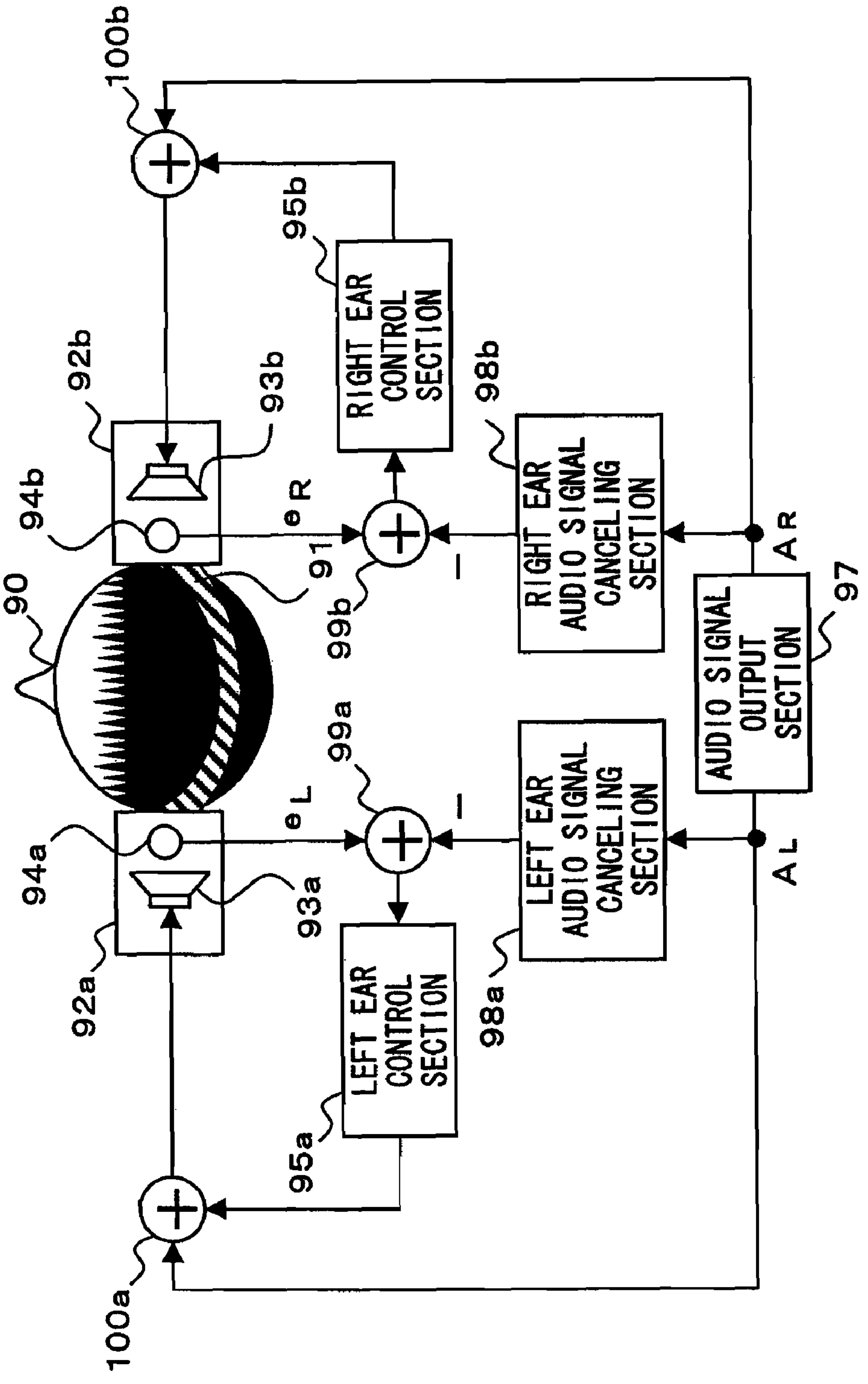
FIG. 22 PRIOR ART
FIG. 22 shows a configuration in which a noise reduction function and an audio signal outputting function are combined.
Figure 23:
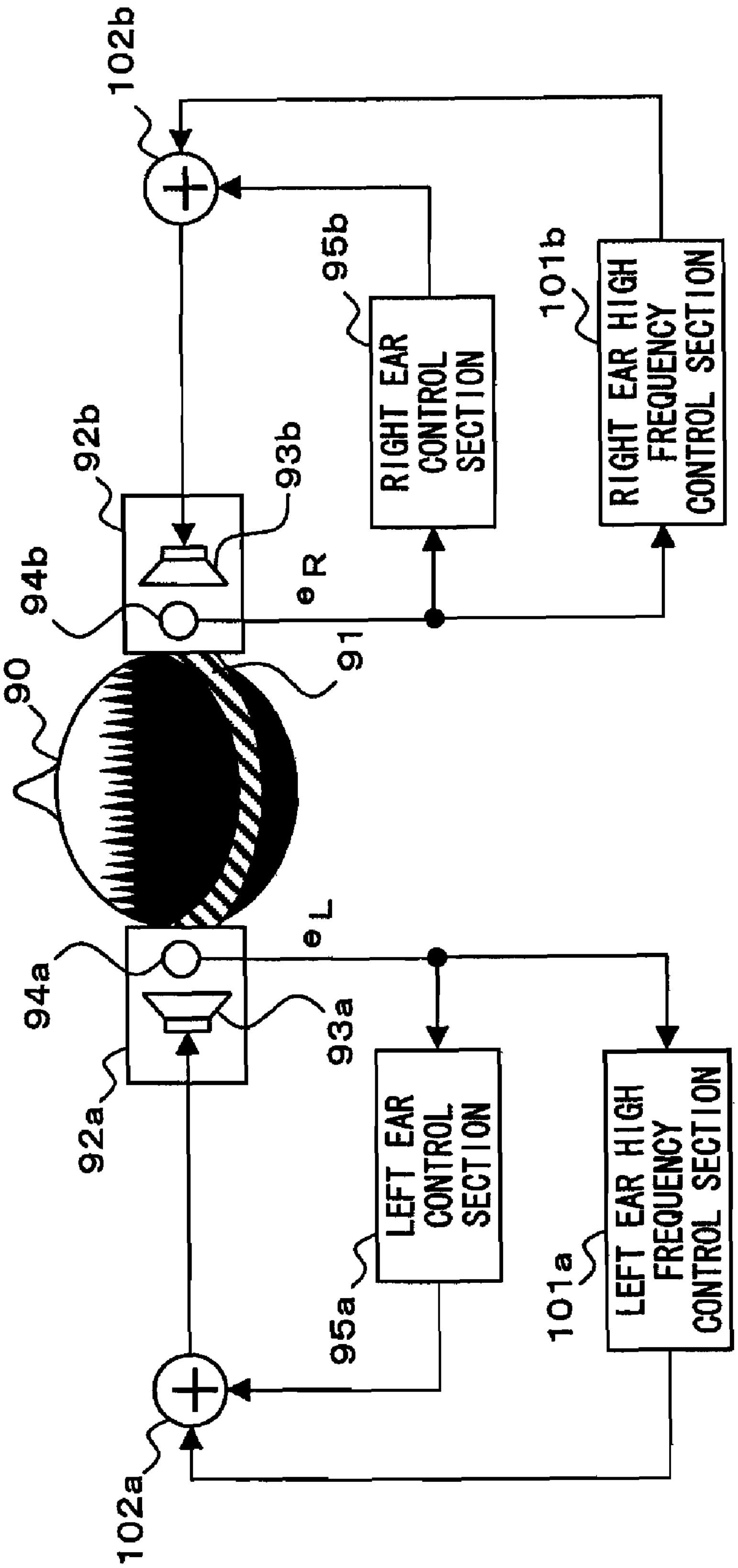
FIG. 23 PRIOR ART
FIG. 23 shows a configuration of a noise-canceling headphone capable of widening a frequency band in which a noise reduction effect can be maintained.

Next, a second use form will be described with reference to FIG. 19. FIG. 19 shows a configuration of the second use form which is further developed from the noise control device according to the second embodiment. The configuration shown in FIG. 19 is a result of adding a control section 15*c* to the configuration shown in FIG. 9. It is assumed for FIG. 19 that components, which are denoted by the same reference numerals as those used for components of the noise control device according to the second embodiment in FIG. 9, have the same functions as those of the components of the noise control device in FIG. 9, and descriptions thereof will be omitted. FIG. 19 shows a view seen from above a head of the user 10. In FIG. 19, the user 10 faces upward.

The control section 15*c* has the same configuration as that of the control section 15*a* described with reference to FIG. 10, except for the filtered X filter 155 for which a filter coefficient simulating the electroacoustic transfer function $H_R$ is set. The control section 15*c* generates, based on the detection signal $e_L$, a control signal for controlling the level of the detection signal $e_L$ detected by the left ear microphone 14*a* such that the level is lowered. The control signal generated by the control section 15*c* is outputted to the adder 21*b*. The control section 15*a* generates, based on the detection signal $e_R$, a control signal for controlling the level of the detection signal $e_R$ detected by the right ear microphone 14*b* such that the level is lowered. The control signal generated by the control section 15*a* is outputted to the adder 21*a*. The adder 21*a* adds the control signal generated by the control section 15*a* to a control signal generated by the left ear high frequency control section 25*a*, and outputs the added signal to the left ear speaker 13*a*. The adder 21*b* adds the control signal generated by the control section 15*c* to a control signal generated by the right ear high frequency control section 25*b*, and outputs the added signal to the right ear speaker 13*b*.

In the above configuration, the left ear high frequency control section 25*a*, for example, is designed by taking the electroacoustic transfer function $H_L$ into account. For this reason, when a characteristic of the left ear microphone 14*a* deteriorates due to aged deterioration or the like, the control signal generated by the left ear high frequency control section 25*a* is not always capable of canceling a noise. As a result, the feedback loop formed by the left ear microphone 14*a*, the left ear high frequency control section 25*a*, the adder 21*a* and the left ear speaker 13*a* does not operate as designed, and this results in a failure to reduce a noise in a high frequency band near the left ear. Similarly, the control section 15*c* is designed by taking into account the electroacoustic transfer function $H_R$ which has the same value as that of the electroacoustic transfer function $H_L$. For this reason, when a characteristic of the left ear microphone 14*a* deteriorates due to aged deterioration or the like, the control signal generated by the control section 15*c* is not always capable of canceling a noise, and this results in a failure to reduce a noise in a low frequency band near the right ear.

However, if the right ear microphone 14*b* does not deteriorate in characteristic, and operates properly, the control section 15*a* and the high frequency control section 25*b* each output a control signal which is capable of canceling a noise. As a result, a noise in a low frequency band arriving near the left ear and a noise in a high frequency band arriving near the right ear can be reduced. As described above, in the configuration shown in FIG. 19, the microphone in the feedback loop including the control section 15*a* is used as the right ear microphone 14*b*, and the microphone in the feedback loop including the control section 15*c* is used as the left ear microphone 14*a*. As a result, even when one of the microphones deteriorates in characteristic, a risk of entirely losing the noise reduction effect can be avoided.

Next, a third use form will be described. A configuration of the third use form is a result of modifying the configuration of the second embodiment shown in FIG. 9 such that the frequency band of the control signal generated by each of the left ear high frequency control section 25*a* and the right ear high frequency control section 25*b* is the same as that of the control section 15*a*. In this configuration, although a frequency band in which the noise is reduced is the frequency band of the control signal generated by the control section 15*a*, the level of noise reduction is further increased.

In each of the noise control devices according to the above-described first to fourth embodiments, components, other than the headband 11, the left ear case 12*a*, the right ear case 12*b*, the left ear speaker 13*a*, the right ear speaker 13*b*, the left ear microphone 14*a*, the right ear microphone 14*b* and the external microphone 14*c*, may be realized as a single chip by using, e.g., an integrated circuit such as LSI or a dedicated signal processing circuit. Also, each of the noise control devices according to the above first to fourth embodiments may be realized by using chips respectively corresponding to the functions of the above-described components. For example, in the configuration shown in FIG. 2, the control section 15 is realized by an integrated circuit. Here, the integrated circuit comprises an input terminal, to which an output from the left ear microphone 14*a* is inputted, and an output terminal for outputting the control signal generated by the control section 15 to the left ear speaker 13*a* and to the right ear speaker 13*b*. Although LSI is mentioned above, the integrated circuit may be referred to as an IC, a system LSI, a super LSI or an ultra LSI, depending on an integration density thereof. The integrated circuit technology is not necessarily limited to LSI. The integrated circuit may be realized as a dedicated circuit or a general-purpose processor. Further, an FPGA (Field Programmable Gate Array), which can be programmed after LSI production, or a reconfigurable processor, which enables connections or settings of circuit cells in an LSI to be reconfigured, may be used. Still further, if a new circuit integration technology to be replaced with the LSI technology is developed as a result of an advance in the semiconductor technology, or is developed based on a technology derived from the semiconductor technology, function blocks may, of course, be integrated using such a technology.

INDUSTRIAL APPLICABILITY

The noise control device according to the present invention is applicable in a headphone apparatus which is capable of, even in the case where processing is performed by a single arithmetic processing circuit, producing a sufficient noise reduction effect without causing an increase in an input/output delay at a control section, and also applicable in a headphone apparatus or the like which has a music playback function.

The invention claimed is:

1. A noise control device for reducing noises respectively arriving in a plurality of spaces which are acoustically independent from each other, the noise control device comprising:

a plurality of sound output means, which are respectively provided in the plurality of spaces so as to respectively correspond to the plurality of spaces, each of the plurality of sound output means for outputting a sound to a corresponding one of the plurality of spaces;

first noise detection means, which is provided in at least one of the plurality of spaces, for detecting a noise arriving in the at least one of the plurality of spaces; and first signal generation means which is a single means for generating, based on the noise detected by one of the first noise detection means, a cancellation signal for canceling the noise, and outputting the generated cancellation signal to each of the plurality of sound output means.

2. The noise control device according to claim 1, wherein the first signal generation means generates the cancellation signal such that a level of the cancellation signal increases in accordance with a decrease in a frequency of the cancellation signal.

3. The noise control device according to claim 1, further comprising:

second noise detection means, provided in a space which is not one of the plurality of spaces and in which a noise source generating the noise is present, for detecting the noise arriving from the noise source; and second signal generation means for generating, based on the noise detected by the second noise detection means, a second cancellation signal for canceling the noise, and outputting the generated second cancellation signal to each of the plurality of sound output means.

4. The noise control device according to claim 1, wherein a plurality of the first noise detection means are provided in the plurality of spaces, respectively, the noise control device further comprises third signal generation means, which are provided respectively corresponding to the plurality of the first noise detection means, each of the third signal generation means for generating, based on the noise detected by a corresponding one of the first noise detection means, a high frequency portion of the cancellation signal having a higher frequency than a predetermined frequency, and outputting the generated high frequency portion of the cancellation signal to one of the sound output means which is provided in a same space as that of the corresponding one of the first noise detection means, and the first signal generation means generates, based on the noise detected by the one of the plurality of first noise detection means, a low frequency portion of the cancellation signal having a frequency no higher than the predetermined frequency, and outputs the generated low frequency portion of the cancellation signal to each of the plurality of sound output means.

5. The noise control device according to claim 4, wherein the predetermined frequency is lower than a frequency at which a phase lag occurs in an electroacoustic transfer function from an input of each of the sound output means to an output of one of the first noise detection means which is provided in a same space as that of the respective sound output means.

6. The noise control device according to claim 1, wherein a plurality of the first noise detection means are provided in the plurality of spaces, respectively, the noise control device further comprises switching means for connecting, among outputs of the plurality of the first noise detection means, an output of one of the first noise detection means to an input of the first signal generation means, and in accordance with an operation, the switching means connects the input of the first signal generation means to the output of the one of the first noise detection means that is provided most closely to a noise source generating the noise.

7. The noise control device according to claim 1, wherein a plurality of the first noise detection means are provided in the plurality of spaces, respectively, the noise control device further comprises:

switching means for connecting, among outputs of the plurality of the first noise detection means, an output of one of the first noise detection means to an input of the first signal generation means; and level detection means for detecting a level of the noise detected by each of the plurality of the first noise detection means, and the switching means connects the input of the first signal generation means to the output of the one of the first noise detection means for which a highest level has been detected by the level detection means.

8. The noise control device according to claim 1, wherein a plurality of the first noise detection means are provided in the plurality of spaces, respectively, the noise control device further comprises:

switching means for connecting, among outputs of the plurality of the first noise detection means, an output of one of the first noise detection means to an input of the first signal generation means; and calculation means for calculating a cross-correlation function for noises respectively detected by the plurality of the first noise detection means, and the switching means connects the input of the first signal generation means to the output of the one of the first noise detection means, based on the cross-correlation function calculated by the calculation means.

9. The noise control device according to claim 1, further comprising:

audio signal output means for outputting an audio signal to each of the plurality of sound output means;

fourth signal generation means for generating a cancellation signal for canceling the audio signal outputted from the audio signal output means; and an adder for adding a signal, which is based on a sound detected by the one of the first noise detection means, to the cancellation signal generated by the fourth signal generation means, and outputting the added signal to the first signal generation means, wherein the signal based on the sound detected by the one of the first noise detection means contains a signal which is based on the noise arriving in the at least one of the plurality of spaces in which the one of the first noise detection means is provided, and contains the audio signal outputted from the audio signal output means via the sound output means provided in the at least one of the plurality of spaces in which the one of the first noise detection means is provided.

10. An integrated circuit for reducing noises respectively arriving in a plurality of spaces which are acoustically independent from each other, the integrated circuit comprising:

an input terminal to which an output from at least one noise detector is inputted, the at least one noise detector being provided in at least one of the plurality of spaces and detecting a noise arriving in the at least one of the plurality of spaces in which the noise detector is provided;

signal generation means which is a single means for generating, based on the output from the at least one noise detector which is inputted to the input terminal, a cancellation signal for canceling the noise detected by the at least one noise detector; and an output terminal for outputting the cancellation signal, which is generated by the signal generation means, to each of a plurality of sound output units which are respectively provided in the plurality of spaces so as to respectively correspond to the plurality of spaces and each of which outputs a sound to a corresponding space.

11. A headphone apparatus for reducing noises respectively arriving in two spaces which are acoustically independent from each other, the headphone apparatus comprising:

left ear sound output means, which is to be provided at a space formed near a left ear of a user, for outputting a sound in the space;

right ear sound output means, which is to be provided at a space formed near a right ear of the user, for outputting a sound in the space;

noise detection means, which is provided in at least one of the two spaces, for detecting a noise arriving in the at least one of the two spaces; and signal generation means which is a single means for generating, based on the noise detected by one of the noise detection means, a cancellation signal for canceling the noise, and outputting the generated cancellation signal to the left ear sound output means and to the right ear sound output means.

* * * * *